US012336905B2

(12) United States Patent
Rahmig et al.

(10) Patent No.: US 12,336,905 B2
(45) Date of Patent: Jun. 24, 2025

(54) STENT AND REPLACEMENT HEART VALVE PROSTHESIS WITH IMPROVED FIXATION FEATURES

(71) Applicant: TRICARES SAS, Paris (FR)

(72) Inventors: Georg Rahmig, Pforzheim (DE); Helmut Straubinger, Aschheim (DE); Coralie Marchand, Munich (DE)

(73) Assignee: TRICARES SAS, Paris (FR)

( * ) Notice: Subject to any disclaimer, the term of this patent is extended or adjusted under 35 U.S.C. 154(b) by 0 days.

(21) Appl. No.: 16/969,750

(22) PCT Filed: Feb. 14, 2019

(86) PCT No.: PCT/EP2019/053633
§ 371 (c)(1),
(2) Date: Aug. 13, 2020

(87) PCT Pub. No.: WO2019/158628
PCT Pub. Date: Aug. 22, 2019

(65) Prior Publication Data
US 2021/0000593 A1 Jan. 7, 2021

(30) Foreign Application Priority Data

Feb. 15, 2018 (EP) ................................. 18000144

(51) Int. Cl.
*A61F 2/24* (2006.01)
*A61F 2/848* (2013.01)
(Continued)

(52) U.S. Cl.
CPC .......... *A61F 2/2418* (2013.01); *A61F 2/2427* (2013.01); *A61F 2/848* (2013.01);
(Continued)

(58) Field of Classification Search
CPC ........ A61F 2/2418; A61F 2/24; A61F 2/9522; A61F 2/2427; A61F 2/848; A61F 2/91;
(Continued)

(56) References Cited

U.S. PATENT DOCUMENTS 6,669,724 B2 * 12/2003 Park ...................... A61F 2/2418
623/1.24
8,070,800 B2 12/2011 Lock et al.
(Continued)

FOREIGN PATENT DOCUMENTS

EP         3202371 A1    8/2017
WO    WO-2010/008548 A2    1/2010
(Continued)

OTHER PUBLICATIONS

International Search Report and Written opinion for International Application No. PCT/EP2019/053633, mailed Mar. 5, 2019 (12 pages).
(Continued)

*Primary Examiner* — Jacqueline Wozincki
(74) *Attorney, Agent, or Firm* — The Dobrusin Law Firm, P.C.

(57) ABSTRACT

Disclosed is an improved stent and a related replacement heart valve prosthesis exhibiting various features for improved fixation and crush resistance. The stent is characterized by an inner stent fixed to an outer stent with connecting struts. The stent and heart valve prosthesis can be used for replacement of a defective endogenous heart valve.

20 Claims, 24 Drawing Sheets

(51) Int. Cl.
    *A61F 2/91*           (2013.01)
    *A61F 2/95*           (2013.01)

(52) U.S. Cl.
    CPC .............. *A61F 2/91* (2013.01); *A61F 2/9522* (2020.05); *A61F 2210/0014* (2013.01); *A61F 2210/0076* (2013.01); *A61F 2220/0033* (2013.01); *A61F 2220/0041* (2013.01); *A61F 2220/0058* (2013.01); *A61F 2220/0075* (2013.01); *A61F 2230/001* (2013.01); *A61F 2250/0039* (2013.01)

(58) Field of Classification Search
    CPC ...... A61F 2210/0014; A61F 2210/0076; A61F 2220/0033; A61F 2220/0041; A61F 2220/0058; A61F 2220/0075; A61F 2250/0039
    See application file for complete search history.

(56) References Cited

U.S. PATENT DOCUMENTS

| | | | | |
|---|---|---|---|---|
| 8,628,571 | B1* | 1/2014 | Hacohen | A61F 2/2403 623/2.18 |
| 9,066,801 | B2* | 6/2015 | Kovalsky | A61F 2/2445 |
| 10,039,639 | B2* | 8/2018 | Marchand | A61F 2/2418 |
| 10,245,143 | B2* | 4/2019 | Gross | A61F 2/2439 |
| 10,543,077 | B2* | 1/2020 | Tuval | A61F 2/2409 |
| 10,702,378 | B2* | 7/2020 | Miyashiro | A61F 2/243 |
| 10,945,839 | B2* | 3/2021 | Alon | A61F 2/2436 |
| 10,952,851 | B2* | 3/2021 | Marchand | A61F 2/2439 |
| 11,109,965 | B2* | 9/2021 | Iyer | A61F 2/2436 |
| 2003/0144725 | A1* | 7/2003 | Lombardi | A61F 2/07 623/1.13 |
| 2004/0093060 | A1* | 5/2004 | Seguin | A61F 2/2418 623/1.11 |
| 2008/0275540 | A1 | 11/2008 | Wen | |
| 2009/0088836 | A1* | 4/2009 | Bishop | A61M 29/02 606/192 |
| 2009/0138079 | A1 | 5/2009 | Tuval et al. | |
| 2009/0240320 | A1* | 9/2009 | Tuval | A61F 2/2436 623/1.24 |
| 2011/0137397 | A1* | 6/2011 | Chau | A61F 2/2409 623/2.37 |
| 2011/0245911 | A1* | 10/2011 | Quill | A61F 2/2418 623/2.11 |
| 2011/0264207 | A1 | 10/2011 | Bonhoeffer et al. | |
| 2012/0022639 | A1* | 1/2012 | Hacohen | A61F 2/2436 623/2.11 |
| 2012/0083874 | A1 | 4/2012 | Dale et al. | |
| 2012/0323316 | A1* | 12/2012 | Chau | A61F 2/2418 623/2.37 |
| 2013/0035759 | A1* | 2/2013 | Gross | A61F 2/246 623/2.38 |
| 2013/0204357 | A1 | 8/2013 | Thill et al. | |
| 2013/0304200 | A1* | 11/2013 | McLean | A61F 2/2412 623/2.18 |
| 2013/0317603 | A1* | 11/2013 | McLean | A61F 2/2427 623/2.12 |
| 2014/0144000 | A1 | 5/2014 | Creaven et al. | |
| 2014/0180401 | A1* | 6/2014 | Quill | A61F 2/2418 623/2.17 |
| 2014/0207231 | A1* | 7/2014 | Hacohen | A61F 2/2418 623/2.11 |
| 2014/0277409 | A1* | 9/2014 | Bortlein | A61F 2/2418 623/2.11 |
| 2014/0331475 | A1 | 11/2014 | Duffy et al. | |
| 2014/0358224 | A1* | 12/2014 | Tegels | A61L 27/06 623/2.14 |
| 2015/0005863 | A1 | 1/2015 | Para | |
| 2015/0039081 | A1* | 2/2015 | Costello | A61F 2/2436 623/2.11 |
| 2015/0081000 | A1 | 3/2015 | Hossainy et al. | |
| 2015/0216661 | A1* | 8/2015 | Hacohen | A61F 2/2457 623/2.37 |
| 2015/0351906 | A1* | 12/2015 | Hammer | A61F 2/2409 623/2.11 |
| 2016/0030169 | A1 | 2/2016 | Shahriari | |
| 2016/0038280 | A1* | 2/2016 | Morriss | A61F 2/2436 623/2.18 |
| 2016/0151153 | A1* | 6/2016 | Sandstrom | A61F 2/2412 623/2.18 |
| 2016/0270910 | A1* | 9/2016 | Birmingham | A61F 2/90 |
| 2016/0331529 | A1* | 11/2016 | Marchand | A61F 2/2436 |
| 2017/0172738 | A1* | 6/2017 | Kassas | A61F 2/2409 |
| 2017/0181852 | A1* | 6/2017 | Kassas | A61F 2/2418 |
| 2017/0216027 | A1 | 8/2017 | Marchand et al. | |
| 2017/0231761 | A1 | 8/2017 | Cohen-Tzemach et al. | |
| 2018/0055629 | A1 | 3/2018 | Oba et al. | |
| 2018/0147053 | A1* | 5/2018 | Tuval | A61F 2/2412 |
| 2018/0185142 | A1* | 7/2018 | Quill | A61F 2/2436 |
| 2018/0338832 | A1 | 11/2018 | Ganesan et al. | |
| 2019/0167421 | A1* | 6/2019 | Chau | A61F 2/2418 |
| 2019/0262129 | A1* | 8/2019 | Cooper | A61F 2/2409 |
| 2019/0321171 | A1* | 10/2019 | Morriss | A61F 2/2409 |
| 2019/0365538 | A1* | 12/2019 | Chambers | A61F 2/2418 |
| 2020/0315794 | A1* | 10/2020 | Quill | A61F 2/2436 |
| 2021/0000593 | A1 | 1/2021 | Rahmig et al. | |
| 2021/0196459 | A1 | 7/2021 | Marchand et al. | |
| 2021/0315691 | A1 | 10/2021 | Rahmig et al. | |

FOREIGN PATENT DOCUMENTS

| | | |
|---|---|---|
| WO | WO-2012/178115 A2 | 12/2012 |
| WO | WO-2015/107226 A1 | 7/2015 |
| WO | WO-2018/197041 A1 | 11/2018 |
| WO | WO-2019/158628 A1 | 8/2019 |

OTHER PUBLICATIONS

International Search Report and Written Opinion for International Application No. PCT/EP2015/051037, mailed May 6, 2015 (9 pages).

International Search Report and Written Opinion for International Application No. PCT/EP2019/073768, mailed Dec. 13, 2019 (10 pages).

International Search Report and Written Opinion for International Application No. PCT/EP2019/075216, mailed Feb. 7, 2020 (10 pages).

International Search Report and Written Opinion for International Application No. PCT/EP2020/051955, mailed Mar. 26, 2020 (12 pages).

* cited by examiner

* different types of loops a)

b)

c)

a)

b)

a)

b)

STENT AND REPLACEMENT HEART VALVE PROSTHESIS WITH IMPROVED FIXATION FEATURES

The present invention relates to a stent and a replacement heart valve prosthesis exhibiting improved fixation and implantation features.

In the last decades minimally invasive techniques have advanced and are now feasible in many medical fields.

In a number of medical fields it is now possible to treat patients by minimally invasive techniques allowing for the treatment of such patients who could otherwise not be adequately taken care of due to their physical condition and the risks connected with surgery. Many of such minimally invasive methods apply delivery systems, e.g. catheters, for implanting the medical device to a desired target site.

In particular, in recent years the treatment of heart valve diseases and defects has become more and more successful. Examples are transapical, transjugular and transfemoral procedures for heart valve replacement therapies, e.g. aortic or mitral heart valve treatments.

In many cases a stent-based prosthesis with a tissue based replacement valve is used and implanted to replace the native heart valve. The replacement heart valve is placed into the patient at the target site in a controlled and coordinated manner by way of a catheter delivery system.

The replacement heart valve has to be crimped and loaded onto the catheter system. The delivery system is then introduced into the patient's vasculature, e.g. transfemorally, and directed to the target site. At the target site the replacement heart valve prosthesis has to be positioned very precisely before its final release from the catheter in order to achieve a correct deployment. A correct and precise positioning is essential for the successful functionality of the implanted device as well as a long-term correct fixation at the target site.

Finally not only the correct site has to be reached but it is also desirable that a specific three dimensional positioning is achieved including inter alia the position as such, a certain angle and uniform distances from the native tissue in e.g. a cavity.

Equally important is a long-term fixation of the replacement heart valve prosthesis at the target site with respect to the above described aspects, and particularly before any tissue may grow into the prosthesis supporting a long-term and stable fixation at the implantation site.

Hence there exists a need for a prosthesis which cannot only be correctly positioned but which also is exhibiting features supporting a long-term fixation and avoiding displacement during the heart function and in particular heart contractions.

One problem in known replacement heart valves is that the medical device can be placed at the desired target site with good precision, however, that due to the patient's heart beating shortly after the implantation, e.g. some days or weeks thereafter, the implanted prosthesis dislocates and thus causes a malfunctioning of the prosthesis as such. More so the dislocation can be lethal for the patient.

In particular this issue causes a problem in replacement heart valve technology wherein replacement heart valves are confronted with a rather soft tissue environment. In such circumstances the implanted prosthesis tends to dislocate due to e.g. the soft tissue context and the limited radial forces of the replacement heart valve prosthesis.

More particularly, it is a problem, e.g. in tricuspid or mitral replacement heart valve technology, wherein the diameter of the valve is large, and the annulus and atrial and ventricular tissue surrounding the heart valve is very soft.

Thus in known replacement heart valve prostheses there exists the danger of displacement or that either a too low or a too high radial force is produced by the prosthesis either leading to displacement of the prosthesis in vivo or leading to an interference of the replacement prosthesis with the natural heart function.

Accordingly, it is one object of the current disclosure to provide a means allowing for better fixation of a replacement heart valve prosthesis, or at least to achieve reducing the disadvantages of the prior art or essentially avoiding these disadvantages.

It is another object of the current disclosure to furnish a heart valve replacement prosthesis providing for fixation means supporting the correct fixation and maintaining a correct positioning immediately after the implantation thereof, or at least reducing the disadvantages of the prior art or essentially avoiding these disadvantages.

It is another object of the current disclosure to provide a variation of a solution for an advantageous or improved fixation of a stent or/and a replacement heart valve prosthesis. In particular such a prosthesis shall be useful for tricuspid or/and mitral replacement heart valve therapies.

Another particular object of the current disclosure is material or/and design variations in a two part stent or two part replacement heart valve prosthesis which allows for advantageous fixation at the target site.

In particular interest is another object wherein a replacement heart valve prosthesis is provided wherein two prefabricated parts are connected in a releasable, e.g. by way of a connecting means, or non-releasable way, e.g. by way of welding, riveting or suturing to form a unit of a replacement heart valve prosthesis which allows for advantageous fixation at the target site.

It is another object of the current disclosure to provide a stent or/and a replacement heart valve prosthesis exhibiting features for a facilitated or/and advantageous cost effectiveness with regards to its production.

It is yet another object of the current disclosure to provide atraumatic fixation means useful in replacement heart valve prostheses.

BRIEF SUMMARY OF THE DISCLOSURE

In one aspect the disclosure relates to a stent or replacement heart valve prosthesis exhibiting advantageous fixation characteristics.

In another aspect the disclosure relates to the replacement of a defect endogenous heart valve wherein the endogenous heart valve is a tricuspid heart valve, or a mitral heart valve.

In another aspect the disclosure relates to a method of replacement of a defect endogenous heart valve or the implantation of a replacement heart valve prosthesis in a person experiencing impaired heart valve function.

In another aspect the disclosure relates to a stent or replacement heart valve prosthesis characterized by an inner stent fixed to an outer stent wherein both stents are laser cut or wherein the outer stent is a mesh stent, and preferably the stents are made of Nitinol.

In another aspect the disclosure relates to a replacement heart valve prosthesis comprising various features useful for an improved fixation of said prosthesis in a heart in its target site.

In another aspect the disclosure relates to providing means useful for the improved fixation of a replacement heart valve prosthesis in a heart in its target site.

In another aspect the disclosure relates to a connecting means for stents.

BRIEF DESCRIPTION OF THE DRAWINGS

Preferred embodiments of the disclosure are exemplified by the Figures wherein:

FIG. 3b depicts a cut of the prosthesis and thus the inner stent (2) is visible.

FIG. 14a, b, c illustrates one aspect of the disclosure, wherein the sequence of closing of clipping means (19) is depicted.

In FIG. 14 b) the interlocking nail (9) of the connecting strut (12, 12') of the other stent (and counter connecting strut) is introduced into the interlocking yoke (18) which provides for a stable connection of the two laser cut stents. The stable connection by way of the two parts (9) and (18) is achieved by its specific geometry of the interlocking parts. This geometry may vary and it is not restricted to the geometry depicted here.

FIG. 14 c) illustrates the final connection of the connecting struts (12, 12') of the two laser cut stents. Sleeve (10) is pushed over the interlocked parts (18) and (9) wherein the sleeve (10) secures the fixation by interaction with the distal part of interlocking yoke (18). The sleeve (10) can be released when the two distal parts of interlocking yoke (18) are pushed together and thus the sleeve (10) can be pushed again over one connecting strut (12'). At the end of part (18) a stop means prevents that sleeve (10) from moving too far over the interlocking means (18) and (9). The interlocking yoke end prevents movement of the sleeve, at least in one or in both directions along the connecting struts.

FIG. 17 is a schematic drawing of the photo (FIG. 18) of the inventive laser cut stent in stent prosthesis according to the disclosure. The dark line shows the proximal area (20), the faint line shows the middle and distal areas (22/23) of FIG. 12. In FIG. 17 it is shown that even though a stress impacts onto the prosthesis the inner stent is not impacted and the valve can properly function and its functionality is maintained which is highly advantageous. FIG. 17 simulates the behavior of the laser cut stent in stent prosthesis according to the disclosure: even if the laser cut stent in stent prosthesis in the middle and distal areas are subject to strong deformation stress, such a stress impact will preferably only be transferred to the proximal area in a lesser degree. Also, this stress impact will not arrive at or impact the inner stent carrying the valve. This is partly or essentially due to the positioning of the connecting means in this area. When the heart beat impacts on the laser cut outer stent (11) one goal is to maintain an optimal geometry of the valve carrying part of the replacement heart valve prosthesis (the inner stent (2)) while at the same time provide for an advantageous fixation of the prosthesis. The inventors have found a design using two laser cut stents characterized by a special connecting means and design which can essentially achieve to maintaining the inner stent (2) carrying the valve at essentially its original geometry. At the same time such a design provides for an advantageous fixation of the replacement heart valve prosthesis in the target site after implantation.

Figure 17:
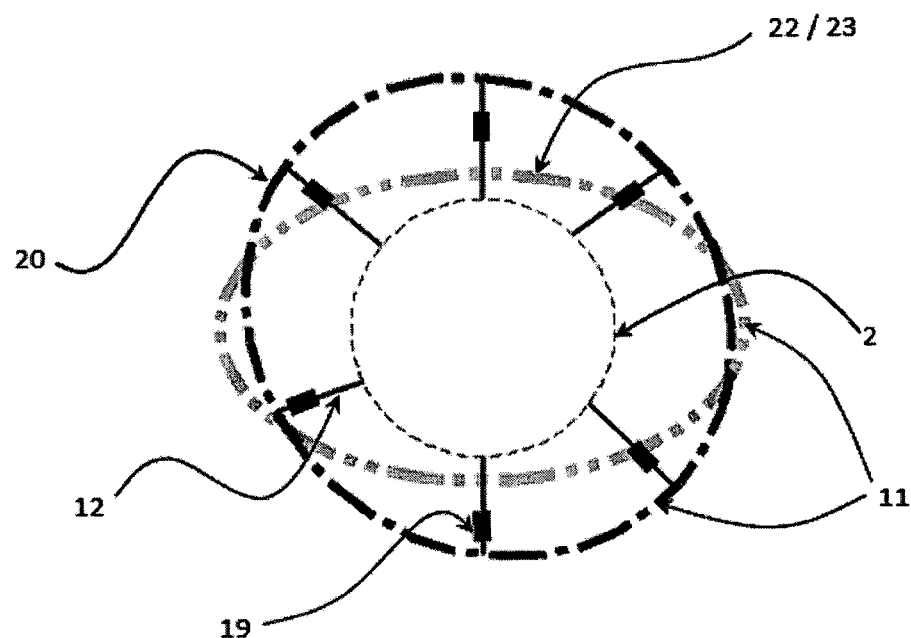
FIGS. 17 and 18 illustrate one aspect of the disclosure, i.e., the deformation of the outer laser cut stent during heart beating in vivo and the conservation and maintenance of the original round geometry of the laser cut inner stent carrying the valve. The inventive design of two laser cut stents, preferably Nitinol stents, which are connected at predefined positions by inventive connecting means advantageously achieves correct positioning of the prosthesis at the target site, good fixation characteristics and essentially leakage free functioning of the valve fixed to the laser cut inner stent. The inventive design using two laser cut stents with a predefined connection of the two stents provides for an advantageous crush resistance allowing for correct valve function of the replacement heart valve prosthesis.
Figure 18:
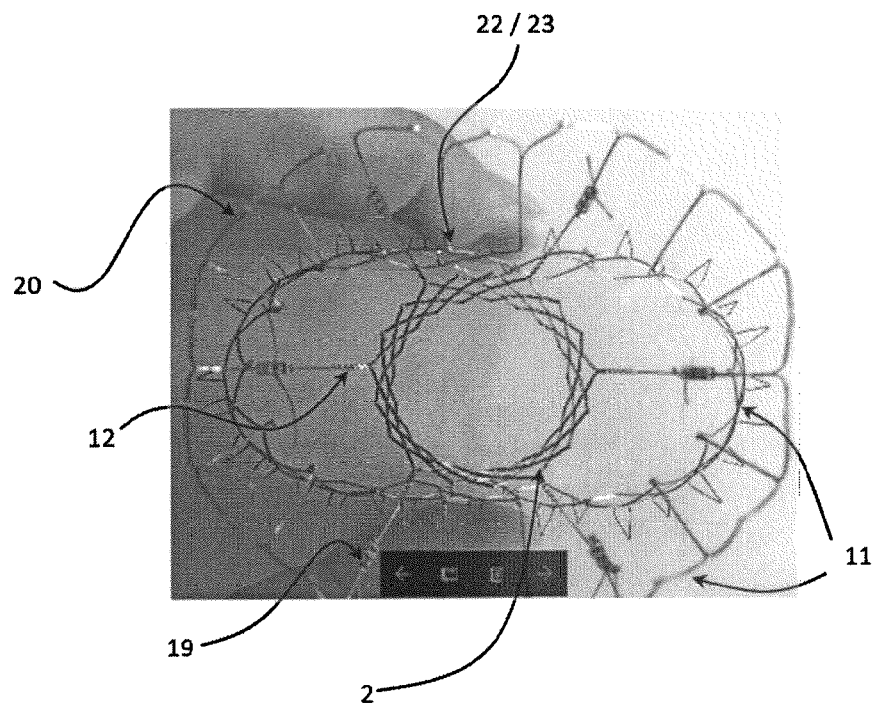

As depicted in both FIGS. 17 and 18 the laser cut outer stent (11) is flexible and maintains thus its contact with the surrounding tissue at its implantation site in the heart. It thus exhibits a good compliance with the endogenous surrounding tissue. Moreover, in this manner the outer stent of the prosthesis maintains the most possible friction with the tissue contributing together with other aspects of the prosthesis to an advantageous fixation. At the same time the laser cut inner stent (2) carrying the valve maintains essentially its round shape and accordingly an optimal geometry for optimal valve function. In particular the deformation and maintenance of contact with the heart tissue can be seen in the middle and distal area (22/23) of the laser cut outer stent. The proximal area (20) is less or not at all subject to deformation. The connecting struts (12) and the connecting means (19) provide for a stable connection of the laser cut inner and outer stents. At the same time these structures advantageously contribute to the shock isolation of the inner laser cut stent from the outer laser cut stent of the prosthesis. Moreover, the positioning of these elements (12) (19) provide for an advantageous crush resistance and a reduced deformation of the laser cut inner stent. Moreover, the S-struts (8) in combination with the connecting means (19) and their specific orientation and positioning within the replacement heart valve prosthesis support a positive crush resistance and the maintenance of the laser cut inner stent in an essentially round shape and essentially optimal valve function geometry.

Figure 19:
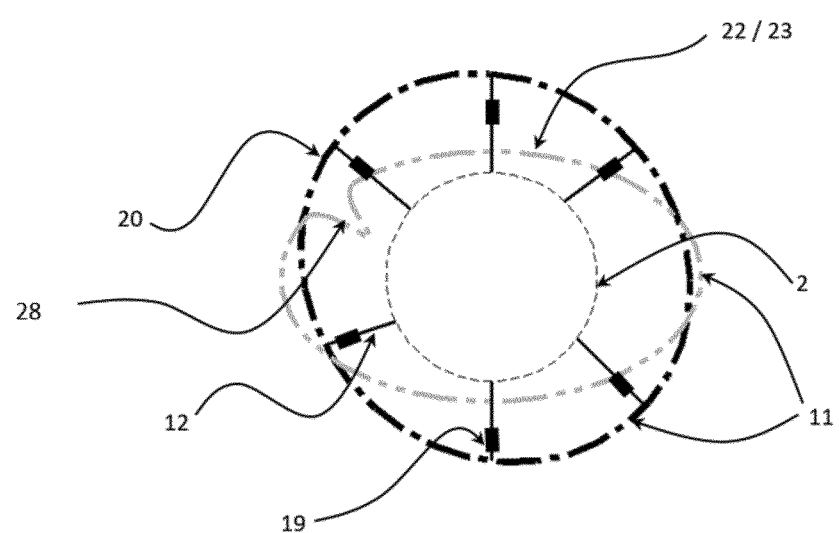

FIG. 19 illustrates one aspect of the disclosure, wherein a folding (28) of the outer stent after release is depicted. Such a folding shall be avoided and the design according to the disclosure herein supports the prevention of such a disadvantageous folding and malfunctioning of a replacement heart valve prosthesis.

Figure 20:
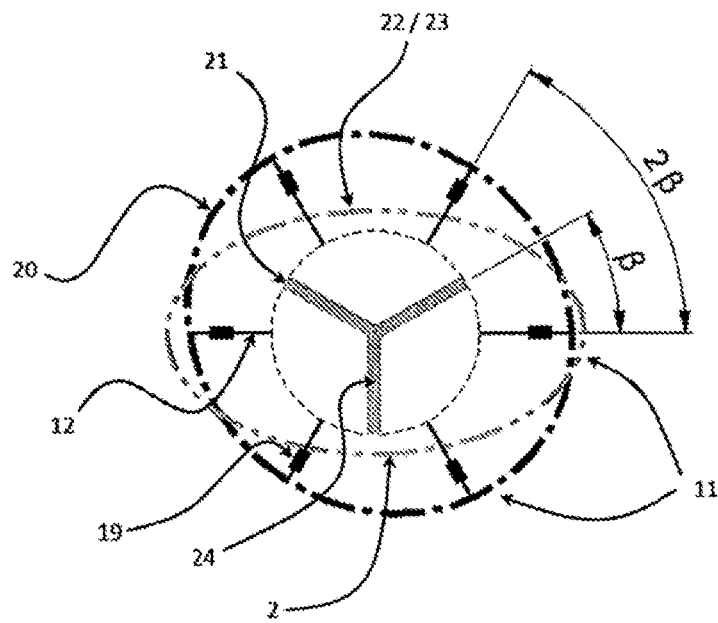
Figure 21:
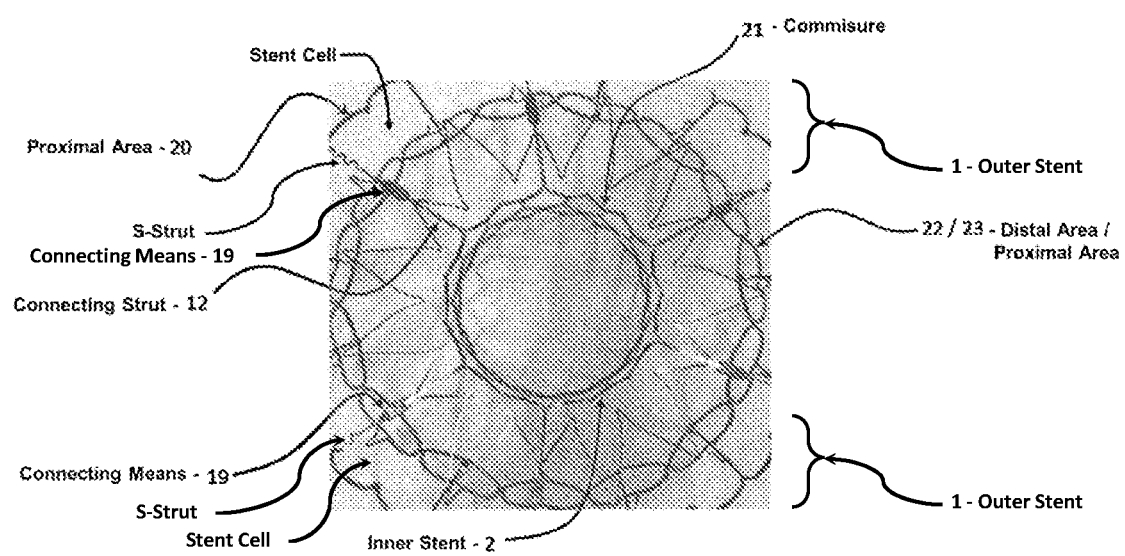

FIGS. 20 and 21 illustrate one aspect of the disclosure, wherein the particular positioning and orientation of the laser cut inner and outer stent and connecting struts (12) and connecting means (19) are described.

Figure 22:
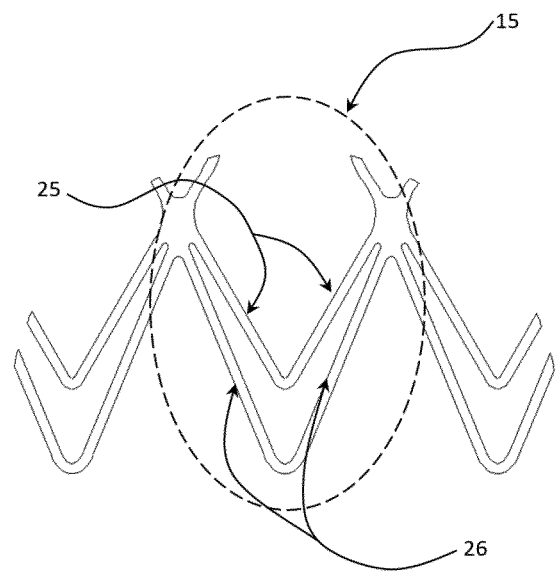

FIG. 22, 23, 24 illustrate one aspect of the disclosure, wherein the anchoring cells (15) and fixation loops are depicted in different embodiments and designs.

Figure 25:
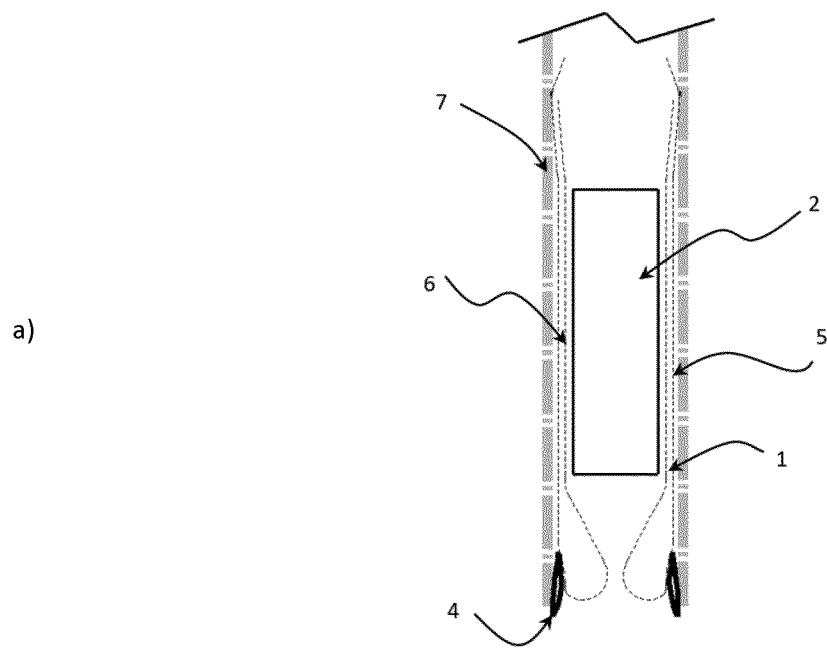
Figure 25:
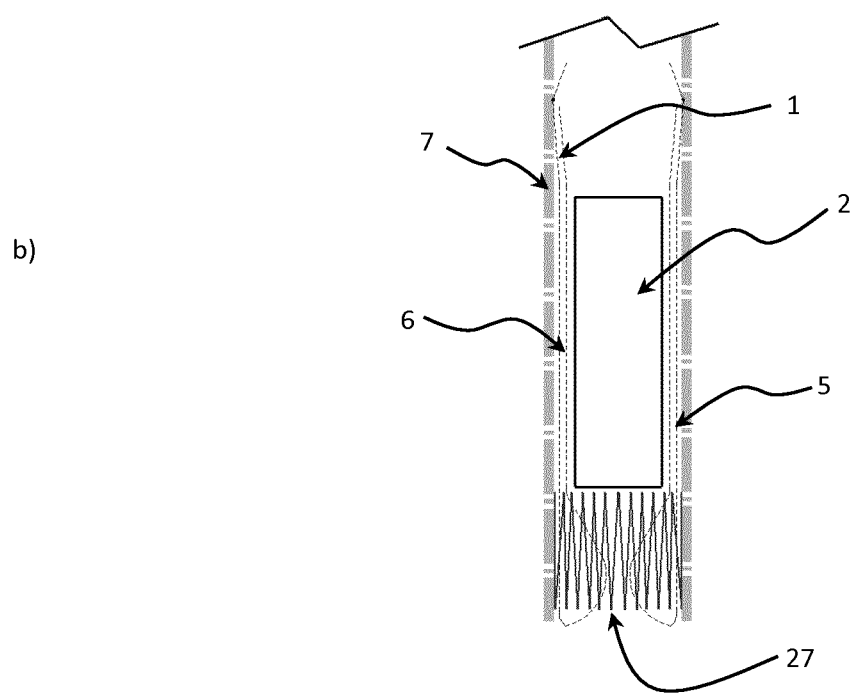

FIG. 25a illustrates one aspect of the disclosure, i.e. a laser cut stent in a mesh stent of a replacement heart valve prosthesis according to the disclosure re-loaded into a catheter. The advantage of the loop design according to the disclosure is the flexibility of the loops (4) and their special design allowing for retrievability into the catheter shaft by way of flipping over during the retrieval or re-loading procedure.

FIG. 25b illustrates one aspect of the disclosure, i.e. a laser cut stent connected to a mesh stent of a replacement heart valve prosthesis according to the disclosure is depicted loaded into a catheter (7). The wire braided outer stent (1) with inner mesh (6) and outer mesh (5) connected to inner stent (2) is illustrated wherein a Z-ring (27) is connected to outer mesh (5). Furthermore, it is apparent from this Figure that the wire braided outer stent (1) elongates during loading and the Z-ring (27) is not superimposed with inner stent (2) but arrives at a position distal from the inner stent (2) which advantageously helps to reducing the catheter diameter.

Figure 14:
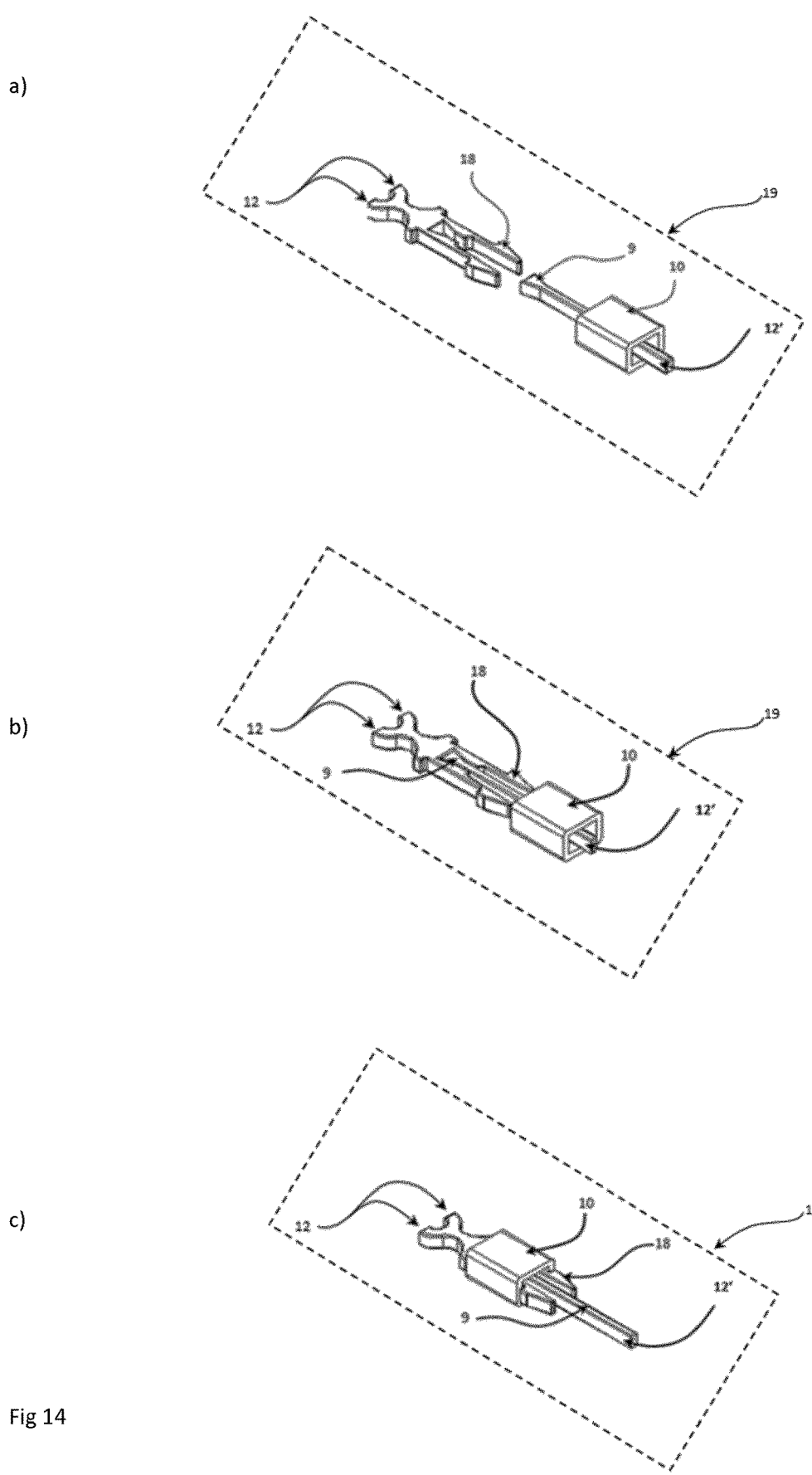
In FIG. 14 a) interlocking yoke (18) is shown connected to either the connecting strut (12, 12') of the inner or outer laser cut stent; and it is depicted in its open configuration ready to receive interlocking nail (9) of the connecting strut (12, 12') of the other stent (either the outer or inner stent representing the counter connecting strut). The counter connecting strut carries the interlocking nail (9), which is introduced through the sleeve (10).
Figure 15:
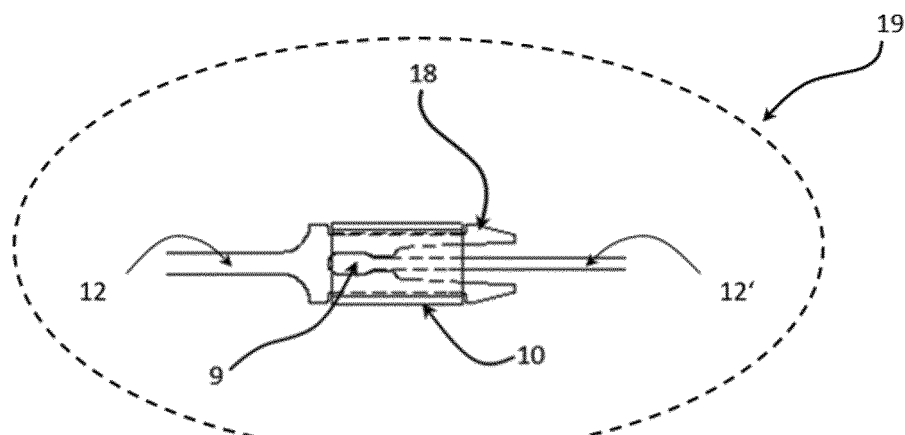
FIGS. 15 a) and b) illustrate a variation of the clipping means (19). The interlocking yoke (18) varies in its design on its distal end. Interlocking yoke (18) is characterized by a different stop design and interaction with sleeve (10) and as regards its release mechanism. In one design in FIG. 15 a) the distal part of (18) is pushed together to release the sleeve (10) while in FIG. 15 b) the distal tips contain springs which need to be pushed inwardly for release. Also interlocking nail (9) has a specific design in each of FIGS. 15 a) and 15 b).
Figure 15:
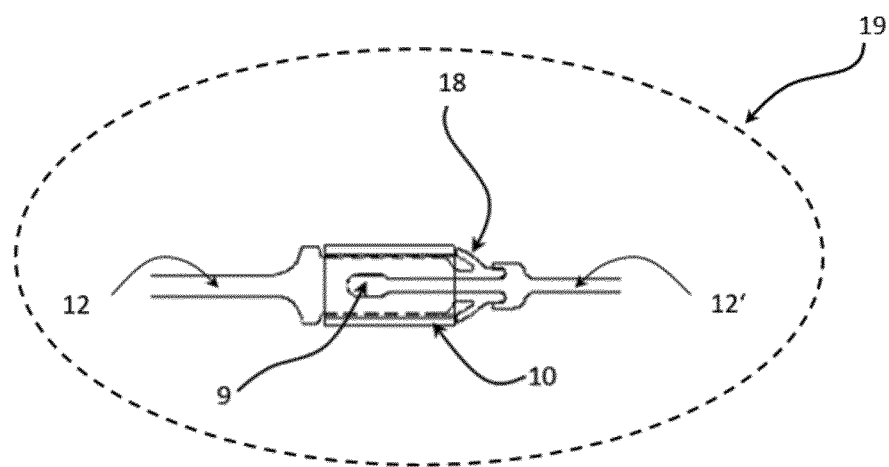
Figure 26:
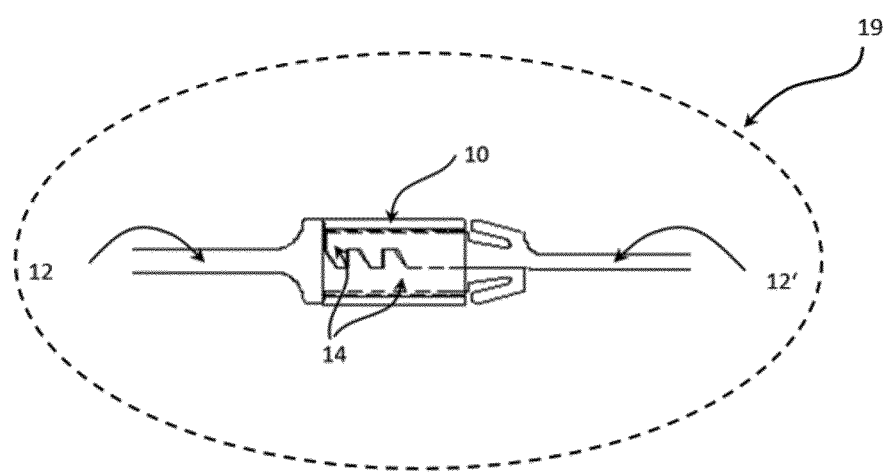

FIG. 26 illustrates one aspect of the disclosure, which is another variation of the connecting means (19) (see also FIGS. 14 and 15). Another embodiment of interlocking teeth (14) are covered by sleeve (10) to connect connecting struts (12, 12').

Figure 27:
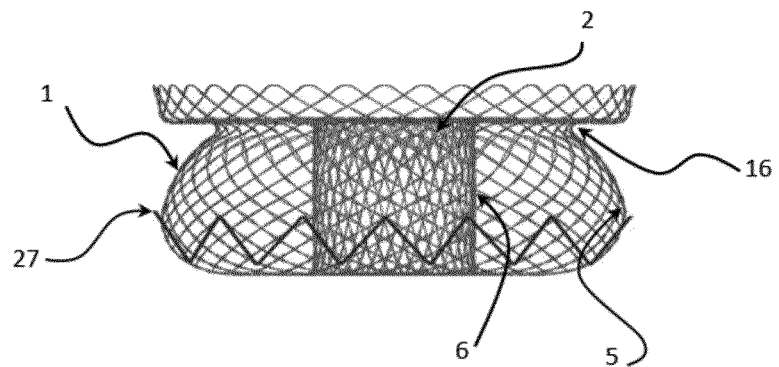

FIG. 27 illustrates one aspect of the disclosure, wherein a laser cut inner stent (2) is connected with an outer mesh stent including a Z-ring (27) connected with the wire braided outer stent (1) on the outer mesh (5). The Z-ring (27) is e.g. sutured outside the outer mesh (5) in the distal area, e.g. at its distal end. The Z-ring (27) combines a stabilizer functionality with a loop functionality. It advantageously contributes to an improved fixation of the replacement heart valve prosthesis in the implantation or target site by inter alia interfering (hooking to or being caught by one or more of the chordae) with the chordae (chordae tendineae) in the ventricle. The Z-ring can be attached to the outer stent by means known to the skilled person, e.g. by suturing, clipping, or other useful means. Advantageously, the Z-ring is formed as a zigzag line wherein the tips formed by said zigzag geometry are directed essentially in proximal and distal direction. The Z-ring is composed of struts; said struts are connected to the outer stent (e.g. outer mesh) essentially in their middle parts and thus the tips of the struts are essentially free and can interfere with the chordae for improved fixation of the prosthesis in the target site of the heard. The Z-ring may also exhibit other useful geometries (still denoted Z-ring herein) like undulating or bent geometries as long as in regular distances tips are comprised by said Z-ring. Also the prosthesis may comprise one, two, three or more Z-rings connected or not connected with each other and/or the outer stent of the prosthesis. Also a groove (16) is depicted.

Figure 28:
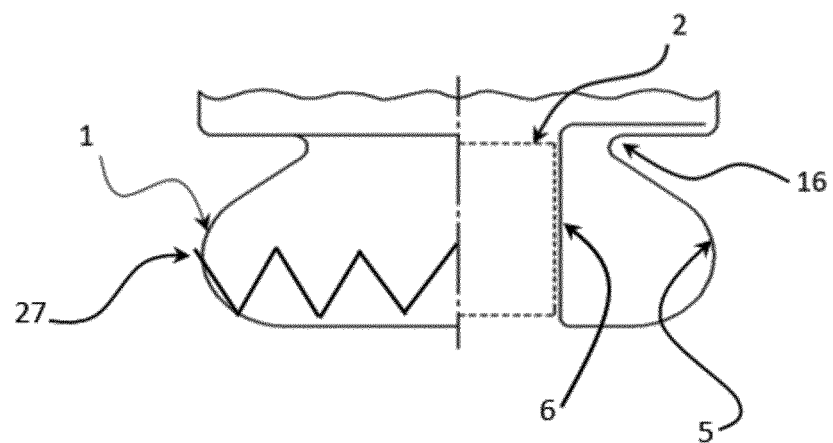

FIG. 28 illustrates one aspect of the disclosure, wherein the prosthesis of FIG. 27 is depicted in a cut representation. The inner stent (2) and braided mesh outer stent (1) is shown as well as a V or U groove (16) which also contributes to the fixation of the prosthesis in the target site. The Z-ring (27) is positioned outside the outer mesh (5) and fixed to it by e.g. sutures. The sutures may be specific to each strut of the Z-ring with two to several sutures per strut, or the suture may start at one position and continue around the stent to arrive at the starting point again. The inner mesh (6) aligns with the laser cut inner stent (2) and is connected therewith, e.g. by suturing. On the left hand side of the Figure one can see one tip of the Z-ring (27) which is characterized by being directed in outward direction and which is not connected with the outer mesh (5). Also the other tips of the Z-ring exhibit the same features.

Figure 29A:
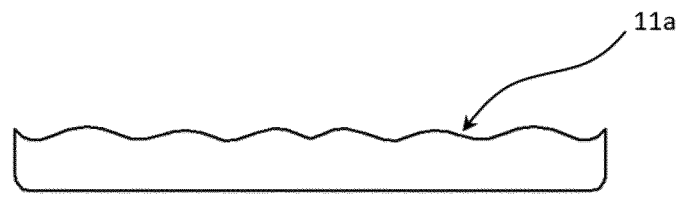
Figure 29B:
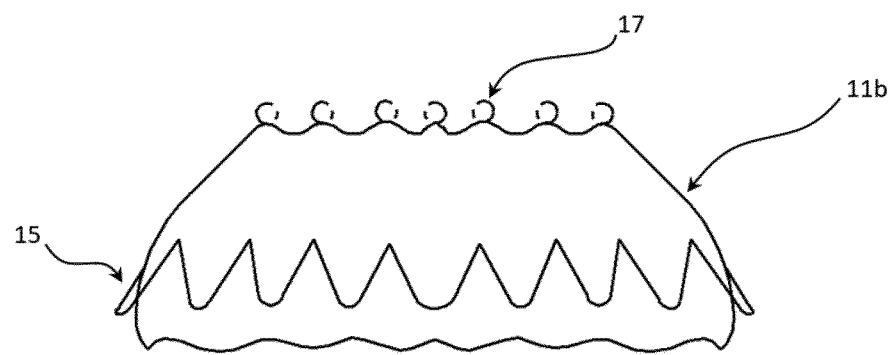
Figure 29C:
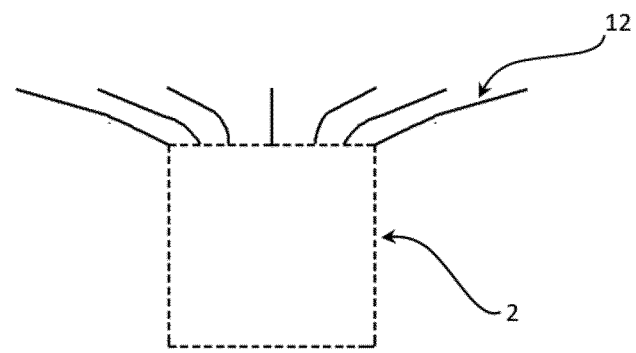
Figure 29D:
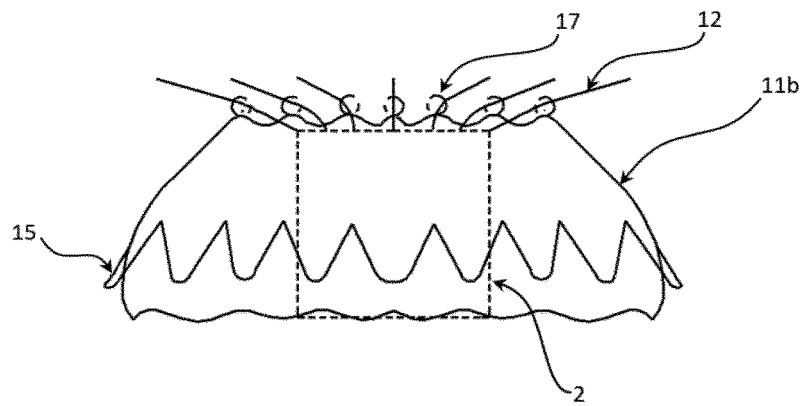
Figure 29E:
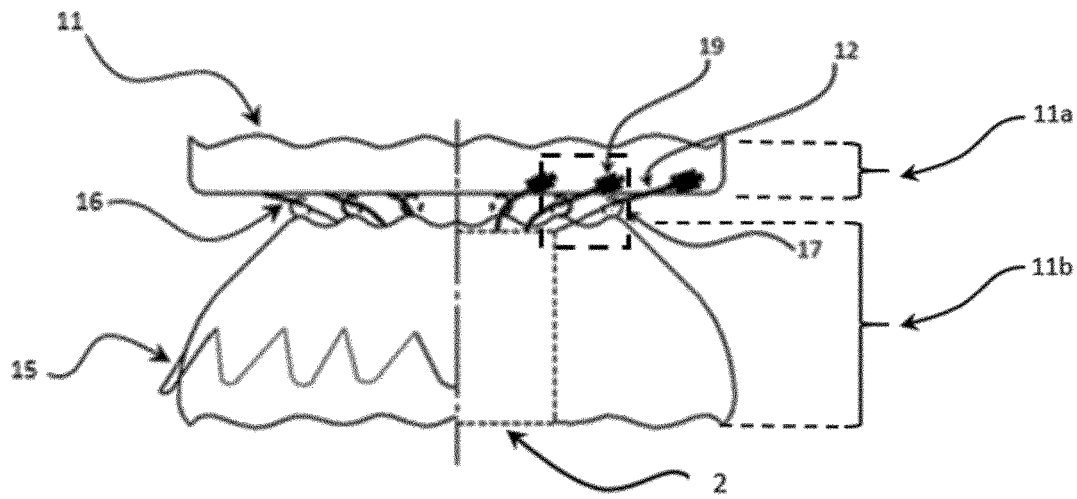
Figure 29F:
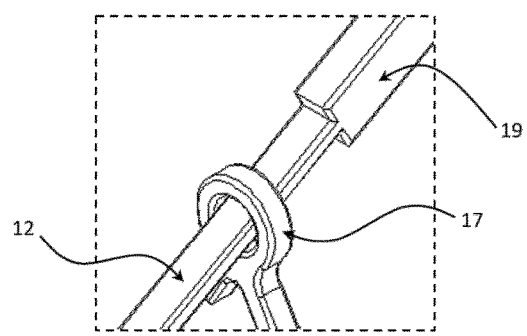

FIGS. 29*a* to 29*f* illustrate one aspect of the disclosure, wherein a cut stent in cut stent replacement heart valve prosthesis is depicted. FIG. 29*f* shows a blow up detail of a connection area and connection means of different stent parts.

FIGS. 29*a* to 29*c* illustrate the three parts of a prosthesis according to the disclosure, i.e. proximal laser cut stent (11*a*), distal laser cut stent (11*b*) including anchoring cells (15) and connecting strut guides (17) and inner stent (2) with connecting struts (12).

In FIG. 29*d* stent parts (2) and (11*b*) are assembled wherein the connecting struts (12) are passed through connecting strut guides (17).

FIG. 29*e* depicts a replacement heart valve prosthesis according to the disclosure wherein a laser cut outer stent parts (11*a*, 11*b*), a V groove (16), an anchoring cell (15), a connecting means (19), connecting struts (12), and connecting strut guides (17) are shown. The laser cut outer stent parts (11*a*, 11*b*) are shown, i.e. a proximal part (11*a*) which will be placed in the atrium of patient and a distal part (11*b*) which will be placed in the annulus/ventricle of the patient during implantation. Accordingly, the prosthesis concerns a three-part stent. The three stents parts (2, 11*a*, 11*b*), respectively, are connected by way of connecting means (19) and connecting strut guide (17).

Of particular interest in this Figure is the area illustrating the interconnection of the different stents or/and of the different stent parts around reference sign (19). This area is depicted and further described in FIG. 29*f*.

The blow up detail FIG. 29*f* (of FIG. 29*e*) shows connecting strut (12), an end part of connecting means (19—the remaining parts of connecting means (19) are not depicted) and connecting strut guide (17). A connecting strut (12) is pushed through connecting strut guide (17) and its end will finally (not shown) be connected to its counterpart connecting strut (12') and connected by connecting means (19) as described above (e.g. FIG. 14, 15, 26). The distal part of connecting strut (12, 19) is designed that it can be easily pushed through the opening or eyelet of connecting strut guide (17). Connecting strut (12) extends from laser cut inner stent (2) (not shown) and connecting strut guide (17) extends from the distal part of the laser cut outer stent (11*b*). The counterpart connecting strut (12'—not shown) extends from the proximal part of the laser cut outer stent (11*a*) to be connected by a connecting means (19—not all parts are shown here) to stably connect the laser cut inner stent (2—carrying the valve—not shown), the laser cut proximal outer stent and the laser cut distal outer stent (11) by way of connecting means (19) and connecting strut guides (17). The special connection design according to the disclosure as described herein provides for advantageous flexibility features of the replacement heart valve prosthesis and supports an improved fixation and functionality of the valve function and thus the prosthesis. Advantageously, the distal area of the prosthesis, in particular the distal area of the outer stent (11*b*), can thus interact very good with the ventricular tissue of the heart and an improved fixation of the prosthesis is achieved. An advantageous compliance of the replacement heart valve prosthesis is achieved. On the other hand also the laser cut inner stent (2) carrying the valve (not shown) is advantageously isolated from the outer stent. Movements or deformations due to heart beating impacting onto the outer stent parts (11*a*, 11*b*) do not transfer to the inner stent (2) and the inner stent (2) thus remains in its favorable geometry and correct valve function is guaranteed. Moreover, the position of the stent parts responsible for connecting the different stent parts (17, 19) in the implanted state is essentially in the annulus region of the target site and hence less impact or stress due to heart beating is achieved as compared to the atrium or ventricle area of the heart where higher forces would impact on the connecting part of the prosthesis. The inventive design as depicted in FIGS. 29*a* to 29*f* also reduces or essentially prevents undesirably longitudinal movement of the prosthesis as such in the target site. The prosthesis replaces the endogenous heart valve function and its replacement valve opens and closes during heart beating. When the valve closes a longitudinal stress impacts on the replacement heat valve prosthesis in proximal direction (in direction to the atrium) and the inner stent (2) is prone to be moved in upward (proximal) direction. More importantly in this context is that the inventive connection design is engineered as well in a manner to prevent longitudinal movements of the inner stent carrying in the replacement heart valve prosthesis the replacement valve. The connection of the three stent parts (2, 11*a*, 11*b*) is advantageously positioned proximally to the inner stent (2). In addition the connecting strut guide (17) has a V shape or as shown here a ring or eyelet used to carry the connection strut (12) originating from the inner stent 2 preventing longitudinal movement of the inner stent when the valve is closed and pressure occurs in proximal direction. At the same time the inventive design characterized by a defined number of connecting means (19) and connecting struts (12) guarantees that the pressure caused by the heart beating and which is squeezing the prosthesis inwardly does essentially not arrive at the inner stent (2). Accordingly, the inner stent (2) remains its essential round shape and advantageous geometry for valve function of the replacement valve attached to the inner stent (2). Connecting strut guides (17) and its special interconnection with the other connecting struts (12) represent an additional means for fixation and holding the inner stent (2) in place and to preventing longitudinal movement thereof within the outer stent (11/11*a*, 11*b*). Thus motion of the inner stent (2) into the atrium is essentially prevented.

Figure 30:
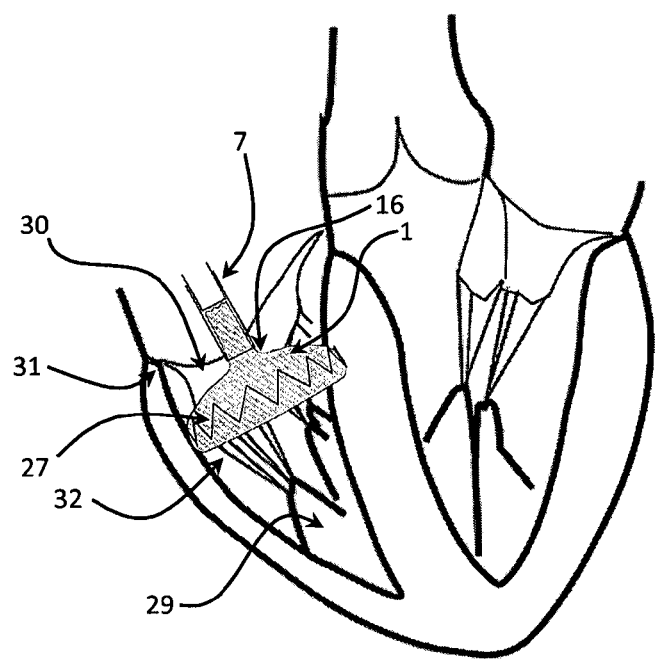

FIG. 30 depicts a replacement heart valve prosthesis according to the disclosure during implantation into a heart target site of an endogenous tricuspid heart valve. The prosthesis is partially released from catheter (7) into the target site wherein the endogenous tricuspid valve (30), annulus (31), chordae (32) and right ventricle (29), the partly released prosthesis (1), V-groove (16) to be released and Z-ring (27) are illustrated during deployment.

Figure 31:
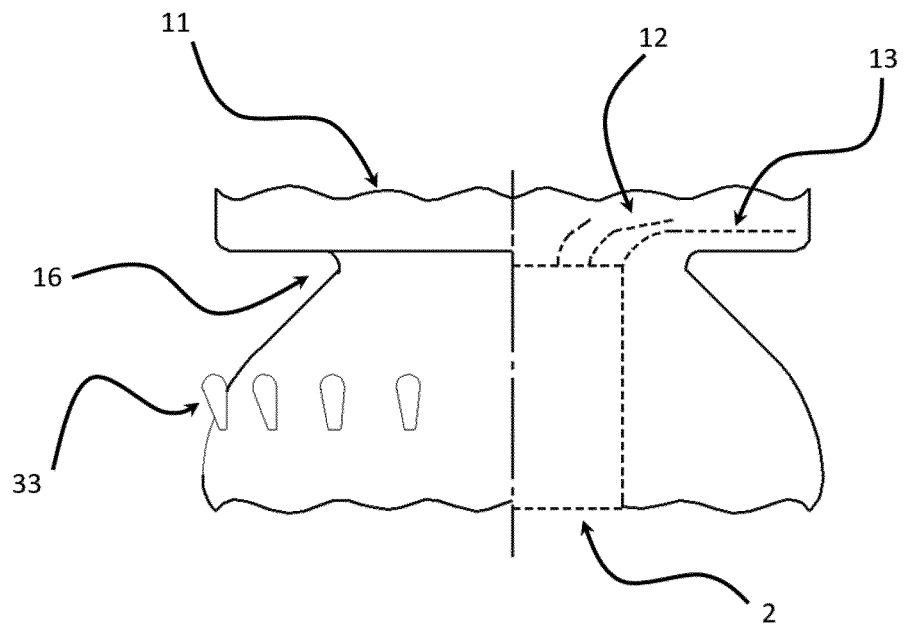
Figure 32:
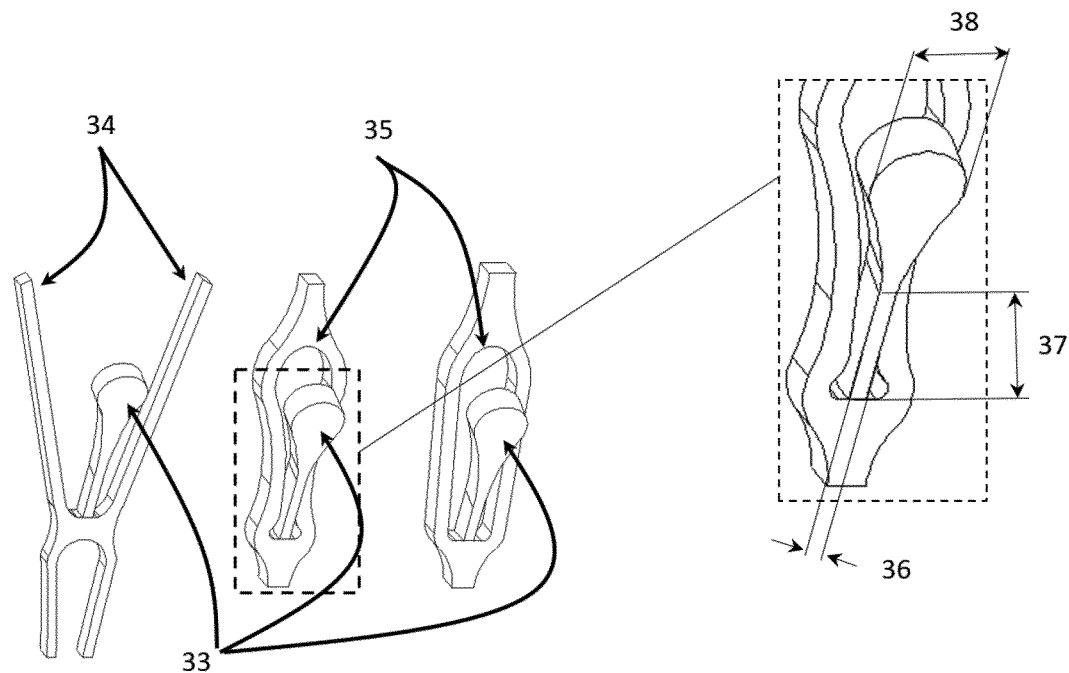

FIGS. 31 and 32 describe another variation of a replacement heart valve prosthesis according to the disclosure.

Figure 9:
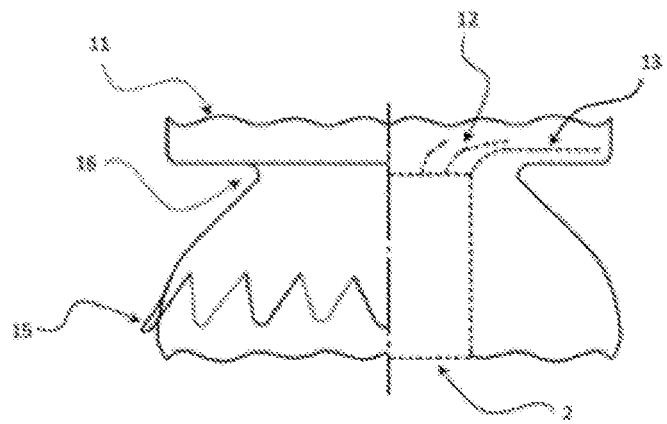
FIG. 9 illustrates one aspect of the disclosure, wherein a laser cut inner stent (2) is depicted within a laser cut outer stent (11). The V-groove (16) is meant to be positioned in the area of the endogenous annulus area when implanted into a patient. In the distal area of the outer laser cut stent (11) anchoring cells (15) are comprised for improved fixation at the target site. The laser cut inner stent (2) and the laser cut outer stent (11) are connected via connecting struts (12) and thus connect inner/outer stent (13) either directly (or by way of a connecting means). The connecting struts (12) can be connected by any useful method known in the art like welding, gluing, riveting, known connecting means or a specially designed connecting means like a clipping means or mechanism. The connecting struts (12) are located in the proximal and annular area.
Figure 10:
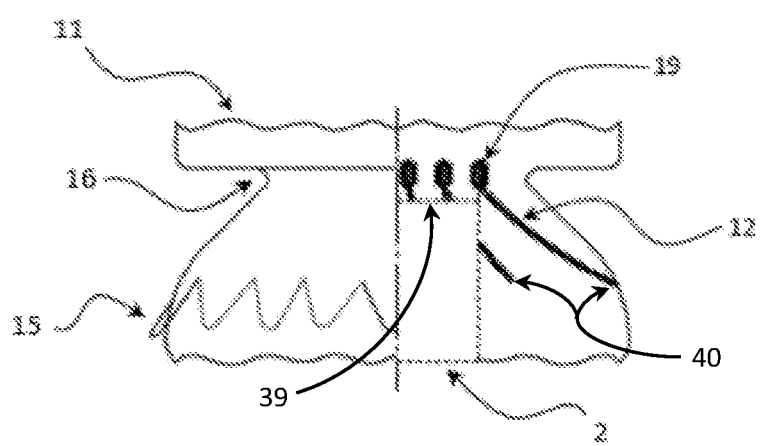
FIG. 10 illustrates one aspect of the disclosure, wherein the connecting struts (12) and connecting means (19) for stable assembling of the two laser cut stents are illustrated. A first connecting strut (12) is connected to the laser cut inner stent (2) in the proximal area at the inflow end (39) by connecting means (19); first connecting strut (12) is shown in FIG. 21. A second connecting strut (12), as labeled in FIG. 10, extends from connecting means (19) and is connected to the laser cut outer stent (11) in the distal area at the outflow end (40). The first and second connecting struts (12) are located between the laser cut inner stent (2) and the laser cut outer stent (11) and may form in this way a double layer in the laser cut outer stent (11). The double wall is in the annulus or sub-annular area or essentially in the ventricular area upon implantation. The connecting means (19) is thus located (after implantation) in the annular area of the implantation site where this area of the replacement heart valve prosthesis is subject to a reduced impact during heart beating. This implies the advantage that one achieves that the connecting means (19) are subject to less stress and impact due to the heart beating.
Figure 11:
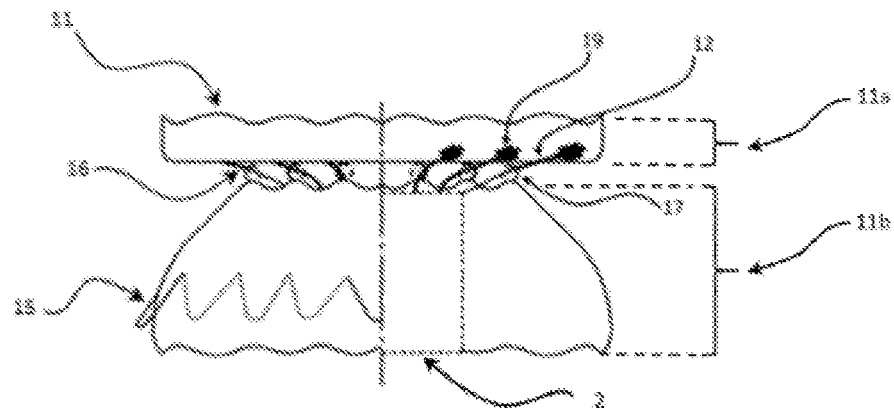
FIG. 11 illustrates one aspect of the disclosure, wherein a variation of the locations of the connecting means (19) is shown. It may be located in the proximal area of the prosthesis. In addition a connecting strut guide (17) is shown. The laser cut stents composing the replacement heart valve prosthesis can be varied in terms of number of connecting means. The prosthesis can be composed of two laser cut stents or three laser cut stent parts wherein a laser cut inner stent (2)(carrying a valve as usually used in the art with three leaflets) is connected via connection means (19) in combination with connecting strut guides (17) with a proximal laser cut outer stent part (11a)(finally placed within the atrium). An additional laser cut outer stent distal part (11b)(finally placed within the ventricle) is connected with the other stent parts by way of connecting strut guides (17). The connecting struts (12) originating from the laser cut inner stent (2) are placed or moved through the connecting strut guides (17) (e.g. one by one). The connecting strut guides (17) originate from the laser cut outer stent distal part (11b) and by way of moving the connecting struts through the connecting strut guides (17) all three stent parts (11a, 11b and 2) are connected at least essentially in the annulus or proximal area when implanted into an individual. The advantage of such a three-part laser cut replacement heart valve prosthesis is improved flexibility and an improved fixation of said prosthesis. The various design features according to the disclosure cooperate to achieve an advantageous improved fixation and reduced longitudinal movement of the prosthesis and its components in the target site. The advantageous flexibility and fixation of the prosthesis as disclosed is characterized after implantation in that the proximal prosthesis part of the outer stent (11 does essentially not move during heart beating. The distal prosthesis part (11b) of the outer stent (11) has an advantageous freedom in movement vis-à-vis the proximal outer stent part (11a) supporting its functionality of an advantageous compliance with the ventricular tissue of the heart. The distal part (11b) of the outer stent (11) can thus move in a coordinated manner with the ventricular heart during heart beating and heart function. One can also denote this increased flexibility as groove, or V-groove, flexibility. It allows for more deformation of the prosthesis in the ventricular outer stent part (11b) which contributes to an improved and correct long-term fixation of the prosthesis in the implantation site (target site).
Figure 12:
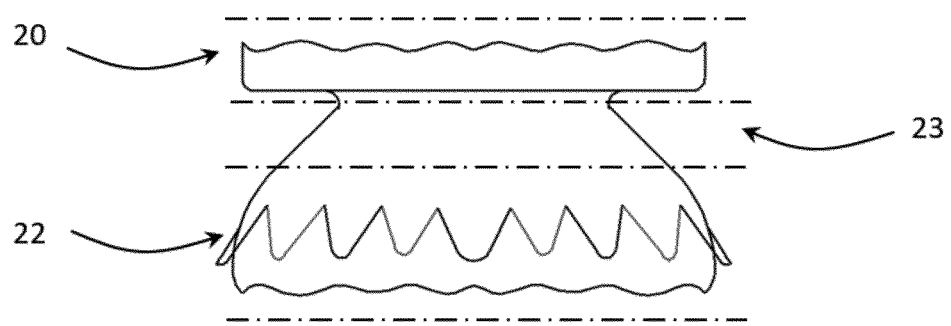
FIG. 12 illustrates one aspect of the disclosure, wherein the different longitudinal areas of the stent in stent prosthesis are shown, i.e. the proximal (20), middle (23) and distal (22) areas. In the distal area loops or anchoring cells are comprised.
Figure 13:
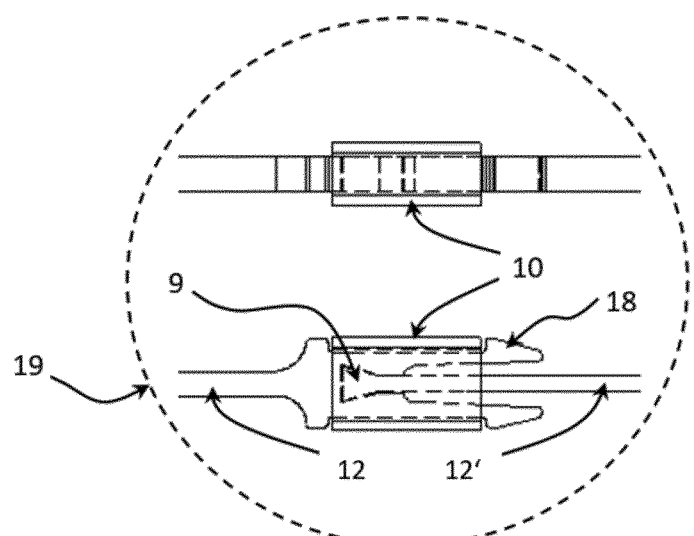
FIG. 13 is a blow up of an embodiment of a connecting means (19) according to the disclosure. It represents one aspect of the disclosure wherein a clipping means is illustrated: the connecting struts (12, 12') are connected by way of said clipping means. It represents a means or device for releasable connection of the connecting struts (12, 12') of the laser cut inner stent (2) and the laser cut outer stent (11). The releasable connection is achieved by interaction of interlocking nail (9), interlocking yoke (18) and sleeve (10).

FIG. 31 is a variation of embodiment described in FIGS. 9, 10 and 11 wherein the loops have a special design as drops (33). The angle of the drops (33) to the middle aye can be 5° to 70°. The number of the drops (33) can vary from 4 to 48 circumferentially, or can be reduced to 10 to 18, or specifically 12. The drops (33) can also be grouped as clusters or/and positioned in different horizontal levels in the outer stent.

FIG. 32 is a detail of the drops wherein the drops (33) have a rounded end shape and can have a round flat end shape which is a special form of an atraumatic design. The drops (33) can be positioned in an open cell (34) or closed window (35). The rounded end shape can have a diameter of from 0.5 mm to 3 mm. The rounded end shape is connected via a strut (drop strut) with the stent and wherein the drop strut can vary in its diameter and also over its length can vary in diameter in order to vary the material and thus adapt the flexibility and hence the force with which each exerts a radial force. It will also be adapted in order to facilitate the loading of the stent in a delivery system. The drop strut dimensions can be 0.1 mm to 0.5 mm wide (36—drop strut width) and 0.25 mm to 15 mm long (37—drop strut length). The drop final part or end can also be called drop, and it may have dimensions of 0.5 mm to 3 mm in diameter (38—drop diameter). Any dimension variation is possible and will be chosen depending on the particular design requirements and target heart dimensions. In this way the flexibility of the drops and the characteristics of anchoring can be tailored and influenced.

DETAILED DESCRIPTION

In the following certain terms of the disclosure will be defined. Otherwise technical terms in the context of the disclosure shall be understood as by the applicable skilled person.

The term "prosthesis" or "medical device" or "implant" in the sense of the disclosure is to be understood as any medical device that can be delivered in a minimally invasive fashion. The terms can be used interchangeably. It can be e.g. a stent or stent-based prosthesis or stent-based replacement heart valve like an aortic heart valve, a mitral heart valve or a tricuspid heart valve.

The term "catheter" or "delivery device" in the sense of the disclosure is to be understood as the device used to deploy a prosthesis in a patient at a determined site, e.g. to replace a heart valve like an aortic heart valve, a mitral heart valve or a tricuspid heart valve.

A "mesh stent" or "braided mesh stent" or "braided stent" in the sense of the disclosure is a stent composed of wires in contrast to a e.g., laser cut Nitinol tube.

A "cut stent" or "laser cut stent" in the sense of the disclosure is a stent which is laser cut from a Nitinol tube.

A "stent area" or "stent areas" in the sense of the disclosure is a defined area of the outer stent, mesh stent or the replacement heart valve prosthesis and in particular it is a longitudinal section or an outer section defined as proximal, middle or distal area.

A "proximal area", "middle area", "distal area" in the sense of the disclosure denotes areas of the stent or prosthesis in relation to the operator performing implantation by use of a catheter wherein proximal is close to the operator and distal is away from the operator. "Middle area" denotes in a stent or prosthesis in the sense of the disclosure the area between the distal and proximal area. The "proximal area" can also be denoted inflow end or inflow area and the "distal area" can also be denoted outflow end or outflow area with regards to the natural blood flow in situ, i.e. in vivo, in an individual (person or patient).

An "annulus area" in the sense of the disclosure is either the respective area of an endogenous heart valve or it defines the respective area in the replacement heart valve or stent which is to be positioned in the implantation site and it meant to align with the endogenous annulus.

A "sub-annular area" in the sense of the disclosure is the area of the prosthesis which is in distal direction (or in outflow direction) of the annulus of the endogenous heart valve. The prosthesis may cover the "sub-annular area" with the grove area and the distal area.

A "groove" in the sense of the disclosure describes an area of the stent or of the prosthesis exhibiting a smaller diameter than other areas and wherein distally and proximally of said groove other areas of the stent or prosthesis having a larger diameter are in neighborhood to said groove; said groove can have a V- or U shape of combinations thereof or other useful geometries.

A "two-part stent" in the sense of the disclosure is composed of an inner and outer stent wherein the inner stent is carrying the heart valve attached to the inner stent, and wherein the inner and outer stents are connected by one or more sutures, a specific mechanism like a click mechanism or any other suitable connecting means forming the replacement heart valve prosthesis. Such a prosthesis in the sense of the disclosure can be suitable or implanted to treat, i.e. to replace, a malfunctioning endogenous heart valve wherein the heart valve is a mitral valve or a tricuspid valve.

In a "three-part stent" in the sense of the disclosure the outer stent is composed of two parts, e.g. made of a laser cut tube, wherein the two parts are connected with the laser cut inner stent carrying the valve by way of a connecting means and a connecting strut guide; a "three-part stent" prosthesis can contain at least three or several, e.g. 4, 5, 6, 7, 8, 9, 10, 11, 12, 13, 14, 15, 16, 17, 18, 19, 20, 21, 22, 23, 24 the connecting means and the connecting strut guides. The connecting strut guides can advantageously be positioned essentially proximal from the inner stent and prevent or limit longitudinal movement of the inner stent.

A "target site" in the sense of the disclosure is the location or place where the replacement heart valve prosthesis is to be implanted and where a dysfunction or malfunction shall be treated.

A "connection" of the stents in the sense of the disclosure is the way of fixation of two stents to each other by way of suturing, by way of a clipping or clicking mechanism or any other useful manner or means to attach the stents to each other.

A "connection means" or "connecting means" in the sense of the disclosure is a mechanical or physical connection of two struts in a stent or laser cut stent wherein two stents are connected to form a stable unit. The connecting means can be by e.g. welding, gluing or any other known procedure or process or means. A connecting means can also be an attachment or clipping means which exhibits a special design and geometry for releasable or non-releasable connection.

"Connection struts" or "connecting struts" in the sense of the disclosure are the struts of two different stents or two different laser cut stents which are used to connect the two stents together. It relates to the struts of the laser cut stent or stents which function is to connect the laser cut inner and outer stent. The connection can be releasable or non-releasable by way of a non-releasable connection or by way of a connection means.

An "anchoring cell" in the sense of the disclosure is a combination of a loop and a stent cell of a laser cut stent wherein the loop is radially moveable and formed in an atraumatic geometry. The "anchoring cell" can be formed as a single unity wherein a stent cell of a laser cut stent or part thereof forms a loop which is radially moveable and formed in an atraumatic geometry.

A "connection strut guide" in the sense of the disclosure relates is used to support or assist in the connection of a three-part stent; the connecting strut guide interacts with the connecting struts. Preferably the connecting struts and the connecting strut guides are positioned in the groove (V or U groove), e.g. about the middle and the proximal area of the distal area. The connecting strut guide ends can be formed as eyelets or in another way to allow a connecting strut to pass through and be connected with its connecting strut counter part. In this manner the proximal part of the stent (prosthesis), the distal part of the stent (prosthesis) and the inner stent will be connected. The middle and distal stent parts of the prosthesis can thus freely move and easily align with the ventricular tissue and its geometry; in this manner the inner stent carrying the valve is decoupled from the outer stent parts of the prosthesis and deformations due to heart beating impact to the outer stent parts of the prosthesis will not reach the inner stent. Thus the inner stent round geometry which is advantageous for a proper valve coaptation and functioning, i.e. correct opening and closing of the valve leaflets, is advantageously guaranteed.

Figure 16:
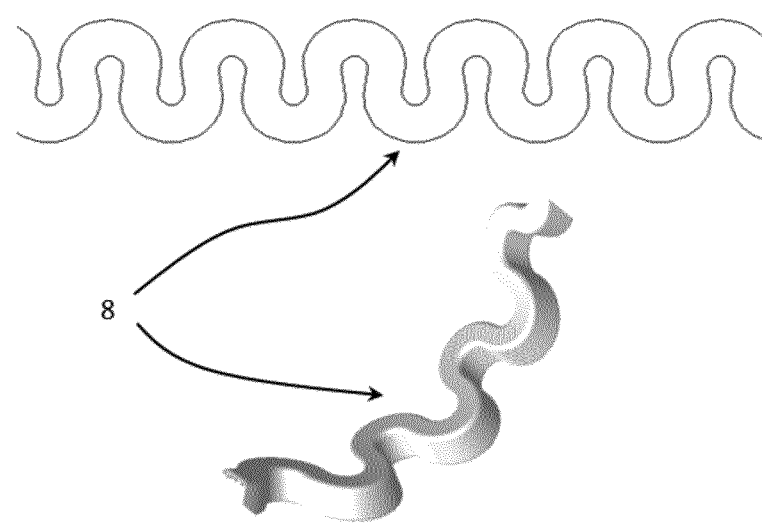
FIG. 16 illustrates one aspect of the disclosure, which relates to a special design of struts used in the laser cut stents of the prosthesis. The S-struts (8) are characterized by an undulating or s-shape geometry. In particular areas of the laser cut stents such S-struts (8) are introduced to achieve a certain flexibility or to isolate movements from one stent to the other stent, e.g., movements effected due to the heart beating received by the outer stent. However, these shocks due to the heart beating is unwanted to be transferred to the inner stent. One goal is to isolate them from the inner stent carrying the valve or/and a deformation of the inner stent potentially impairing a proper valve coaptation or/and functioning. A deformation thus visible in the outer stent shall not be transmitted to the inner stent carrying the valve. The aim is that the inner stent remains essentially in its round geometry which is advantageously for the valve function and in particular for a good coaptation of the valve leaflets.

A "S-strut" or "U-strut or V-strut" in the sense of the disclosure is a stent strut of a laser cut stent, e.g., a Nitinol stent, wherein the strut comprises or is composed of a repeated number of S, U or V units and thus forms a specific geometry which exhibits other characteristics as compared to a straight strut. An exemplary S-strut is depicted in FIG. 16. It may be used together with connecting struts or/and connecting means of the laser cut stents according to the disclosure.

A "loop" in the sense of the disclosure is a means useful for an improved fixation of a stent or prosthesis wherein a loop is fixed to or connected with or forms part of or is an integral part of the outer stent. The "loop" or "loops" in the sense of the disclosure can have different shapes like round, square etc. and are located in a defined area in a defined pattern. A "loop" in the sense of the disclosure will exhibit a defined angle with regard to the outer stent surface and it may be designed that it may flip over when the stent or prosthesis is retrieved into the catheter after an initial and possibly partial deployment. A loop in the sense of the disclosure can be contained in an anchoring cell, and a loop can be formed as a drop.

A "stabilizer" in the sense of the disclosure is a structure which aids for supporting an improved fixation of a stent or replacement heart valve prosthesis at a target site, i.e., at an endogenous heart valve, which is to be replaced. A "stabilizer" can also be understood as a re-enforcement means. The "stabilizer" can support certain characteristics of a stent or prosthesis in the sense of the disclosure, like flexibility or axial force etc., entirely or in a defined area. It can be e.g., an additional wire or stent layer; the "stabilizer" is e.g., at least one Nitinol ring, preferably attached inside or outside of the mesh stent, or combined with or introduced into the mesh of the mesh stent, preferably wherein the at least one Nitinol ring has an undulating, or a V or U geometry, or zigzag geometry, or the "stabilizer" can be designed as a Z-ring.

A "Z-ring" in the sense of the disclosure provides for a fixation functionality, or it combines stabilizer and loop functionalities. Moreover, the fixation or loop functionality advantageously provides for interference with heart structures, e.g., the Chordae of the target site and thus an improved fixation of the prosthesis in the target site is achieved. The prosthesis according to the disclosure may comprise 1, 2, 3, 4, 5, 6 or more Z-rings. Such Z-rings may be interconnected with each other or they may be independently connected with the outer stent, preferably with the outer mesh stent. The Z-ring can be composed of 6 to 50 cells, or 10 to 30 cells, or 15 to 25 cells and/or the strut length of each cell may be in the range of 5 to 15 mm, preferably 8 to 10 mm. The Z-ring may be positioned at any middle or distal area or portion thereof, e.g., it may be positioned at the distal area and preferably at the distal end of the outer mesh stent. The Z-ring can be made of any material which is combinable with the outer mesh stent, and e.g., made of laser cut Nitinol, a wire, a Nitinol wire. The Z-ring can also have any useful geometry like Z, V, U, or zigzag geometry. The Z-ring is preferably a laser cut part and made of Nitinol. The Z-ring is placed place outside the outer mesh stent and may be connected therewith with known means, e.g., suturing, welding, weaving, clipping, or braiding into the mesh stent. The Z-ring may be placed circumferentially around the outer stent. It may also be feasible to design a Z-ring which does not represent a single ring circumferentially around the outer stent but which is composed of single units or parts which are placed around the outer stent. It is also feasible that single Z-ring units or parts are positioned in defined areas of the outer stent in order to be placed in preferred areas vis-à-vis endogenous structures prone for interaction and improved fixation functionality. An important aspect of the Z-ring is that the end parts which are essentially directed distally or proximally are free and unconnected with the outer stent in order to exhibit their fixation function.

An "angle structure" or "angle" in the sense of the disclosure is an angle between two accessory lines drawn at a certain area or stent layer in order to define a certain geometry of said stent layer with regard to other stent structures like the inner stent.

"Angle alpha" or "angle α" in the sense of the disclosure is the angle encompassing two accessory drawing lines of the outer mesh stent each aligned to one outer or inner layer of a mesh stent.

A "spring" or "spring function" or "absorption" in the sense of the disclosure relates to the function of the outer mesh stent when folded as two layers and exhibiting a certain radial force and flexibility which will allow to absorb e.g. movements and shocks from the beating heart and which supports an improved fixation in a soft tissue environment like a tricuspid or mitral valve. The same advantageous effect can be achieved when a laser cut outer stent is used.

A "radial force" in the sense of the disclosure is the force exhibited by a stent or prosthesis in radial outward direction, more particularly the force exhibited by the outer stent of the prosthesis which may be a mesh or a laser cut stent, e.g., a Nitinol stent. The radial force depends on the particular mesh or cut stent design and relates to the material density, e.g., the density of wires per square area in a mesh stent, or the number of cells and size of said cells circumferentially in a certain laser cut stent level or area, e.g., the proximal, middle or distal area. The radial force in a replacement heart valve prosthesis according to the disclosure will be chosen for each area in a magnitude to provide for good contact with the surrounding tissue and to provide good contact therewith. On the other it will be chosen in a magnitude in order to avoid interference with the implantation site and endogenous tissue and function. The radial force may be supported for its fixation function by other means, e.g., loops for fixation.

A "fixation improvement" in the sense of the disclosure describes a better fixation in situ or in vivo as compared to a stent or replacement heart valve which does not exhibit the respective design feature, or in general means in a stent or replacement heart valve supporting the stable and long-term implantation at a desired implantation site.

The term "loading" in the sense of the disclosure is to be understood as positioning a prosthesis onto a catheter in a manner so that the catheter is ready to initiate a delivery and deployment procedure to a patient.

The "target area" in the sense of the disclosure is the three dimensional space surrounding or being within the native organ like a native heart valve which can be e.g. a tricuspid heart valve.

An "atraumatic design" of the loops in the sense of the disclosure is wherein the loops or other means or parts of a stent or a prosthesis are designed to avoid any or essentially any damage of the surrounding tissue or tissue in contact with said parts or at least parts manufactured in a manner to minimize damaging or/and injuring the tissue which they contact.

"Compliance" of the stent or replacement heart valve prosthesis, e.g. comprising an inner laser cut stent within an outer mesh stent, or a laser cut inner stent within a laser cut outer stent, in the sense of the disclosure relates to a positive interference with the target tissue. "Compliance" relates to a design which exhibits good geometry adaptation of the stent or prosthesis to the implantation site and wherein the stent or prosthesis exhibits advantageous fixation characteristics, good functionality as concerns valve function and at the same a minimal interference with the endogenous heart structures and heart function.

"Crush resistance" of a stent or a replacement heart valve prosthesis or a prosthesis in the sense of the disclosure relates to the maintenance of the geometry of the inner stent or/and to the maintenance of the functionality of the replacement valve function due to the design of the outer stent, e.g., a mesh stent or a laser cut Nitinol stent, which provides for a decoupling of inner and outer stent in relation to the impact of the endogenous heart beating to the outer stent of the prosthesis. The positive "crush resistance" of the prosthesis according to the disclosure achieves advantageously the maintenance of the geometry of the inner stent and an essentially correct replacement heart valve function. Particularly advantageous is a radial force of the outer stent to provide for fixation force to the target site and at the same time not to interfere with the endogenous tissue and function. A prosthesis according to the disclosure, e.g., comprising an outer mesh stent, will exhibit punctual deformability while in its entirety still exhibiting radial outward force. At the same time it is deformable to provide advantageous compliance with the ventricular heart tissue. Thus a prosthesis according to the disclosure, e.g., comprising an outer mesh stent, exhibits circumferential outward radial force and punctual deformability for providing advantageous compliance. Thus the crush resistance shall be small which outward radial force is in a magnitude to provide a support and fixation functionality (see, e.g., FIG. 17, 18). The advantage crush resistance of the outer stent advantageously achieves the distribution and reduction of a punctual stress impact in the target area.

In one aspect of the disclosure a or the problem underlying the application is solved by a mesh stent wherein the stent comprises one or more re-enforced areas.

In one aspect of the disclosure the problem underlying the application is solved by a mesh stent comprising one or more fixation loops.

In one aspect of the disclosure the problem underlying the application is solved by a combination of a stent comprising one or more re-enforced areas and one or more fixation loops. Possibly a specific outer stent design exhibiting advantageously the capacity of an alignment with the natural tissue of the transplantation site may support an improved fixation in addition.

Thus according to the present disclosure, it will become possible to provide for a stent or/and a replacement heart valve prosthesis exhibiting advantageous fixation characteristics.

In one aspect the disclosure relates to a mesh stent as described above wherein the one or more fixation loops are characterized by a wire extending from and returning to the stent forming a loop extending outwardly from the stent, preferably in an angle of 10°-90°, or 30°-90°, preferably 50°-60° in proximal direction (in inflow direction), preferably located in the sub-annular area of the stent (ventricular area), preferably wherein a number of loops is located circumferentially of the stent with the same or different distances between each other, or/and are positioned in several rows or levels, or/and are positioned in different rows or/and in alternating positions.

The loops according to the disclosure can be formed in any useful manner and geometry, preferably they are formed as oval, round, open, closed, or/and tapered geometry. Advantageously, the loops have a dimension in the range of 2 mm-15 mm in length, or/and the loops are in the range of 2 mm-10 mm in diameter. The dimensions of a drop are depicted in the figure description and reference number list to which is referred to.

Preferably in the mesh stent according to the disclosure the loops are formed in an atraumatic design. Accordingly, the loops are designed to avoid any damage or essentially any damage of the surrounding tissue or at least manufactured in a manner to minimize damaging or/and injuring the tissue which they contact.

The loops can be positioned as is most useful to increase the fixation characteristics of the prosthesis. Accordingly, the loops can form an angle with regard to the mesh stent in either the proximal or distal direction. In one aspect the mesh stent according to the disclosure exhibits loops designed to flip over in distal direction (in outflow direction) during reloading of the stent into the catheter in situ.

In a preferred aspect the mesh stent according to the disclosure is characterized by a combination of inventive features of the disclosure and wherein the re-enforced area is supported by a stabilizer and/or one, two or more additional mesh layers. The stabilizer can be one, two, three or more stabilizers attached or combined with the mesh stent and preferably the stabilizer is at least one or two Nitinol rings or wires, preferably attached inside or outside of the mesh stent, or combined with or introduced into the mesh of the mesh stent. The stabilizer can exhibit a geometry in different areas or circumferentially the mesh stent, preferably wherein the at least one Nitinol ring has an undulating, or a V or U geometry, or a zigzag geometry.

In one aspect the disclosure relates to an embodiment wherein the outer stent comprises a Z-ring which is positioned outside in the distal area of the outer stent (e.g. a mesh stent), and preferably at the distal end of the outer stent. The Z-ring will advantageously combine a re-enforcement or stabilizer functionality and with its tips protruding essentially in proximal and distal direction it is also characterized by a loop functionality, or a functionality which serves to interfere with heart structures, e.g. the chordae, and thus contributes to an improved fixation characteristics of the replacement heart valve prosthesis as disclosed herein.

In one aspect the disclosure relates to a Z-ring or a number of Z-ring parts useful for supporting or improving a stable fixation of a stent, a two-part stent, a three-part stent of a replacement heart valve prosthesis comprising said stents in a target site, preferably in a heart. The Z-ring or Z-ring parts are characterized by at least two bars and at least one peak or tip in one direction and essentially in counter direction at least two peaks or tips. The number of bars, tips/peaks will vary depending on the overall size of the prosthesis and functional requirements as regards required fixation features.

Such a Z-ring or Z-ring parts are connected to an outer stent of e.g. a replacement heart valve prosthesis in a manner to keep the tips or peaks essentially unconnected with the outer stent and allow their interaction with endogenous structures or tissue which will support improved fixation of the prosthesis. The outer stent may be a mesh stent to which the Z-ring or Z-ring part(s) are connected or interwoven.

The Z-ring or Z-ring parts can be advantageously positioned in the middle or distal area of the outer stent or sub-areas thereof. Preferred are all the bent areas of the outer stent.

In one aspect it is also advantageous if the Z-ring or Z-ring parts are positioned in the distal area of the outer stent of a replacement heart valve prosthesis because such a positioning also implies advantages for catheter diameter because of an advantageous placement of the replacement prosthesis parts, e.g. inner stent, Z-ring or Z-ring parts and the remaining prosthesis parts significant to loading and crimped prosthesis diameter in a catheter (see also in the FIG. 25 b)). In such a manner the Z-ring and the inner stent will be positioned next to each other and not superimposed leading to an increased diameter. Such an advantageous loaded positioning of the prosthesis parts is achieved in advantageously using the elongation of the outer mesh stent in longitudinal direction during crimping and positioning of the Z-ring or the Z-ring parts and inner stent so they achieve a side-by-side position within the catheter.

In one aspect the use of a Z-ring or Z-ring parts will support the concept of an inner stent exhibiting a relative high radial force combined with an outer stent exhibiting relative low radial force and providing a very good compliance with the target site and providing improved or advantageous fixation characteristics of a prosthesis comprising said parts. The Z-ring or Z-ring parts thus make it possible to maintain a relatively low radial force in the outer stent while providing advantageous fixation characteristics.

In an advantageous manner the mesh stent according to the disclosure exhibits reinforced areas wherein the reinforced area(s) is a combination of loops attached to or being an integral part of the outer stent and wherein the mesh stent is reinforced by way of a double, triple or quadruple layer or/and being not connected with the inner stent.

The above features may be combined with an outer mesh stent design wherein the stent area which, when deployed in the target site, will be compliant essentially with the annular or sub-annular area or ventricular area of the target site. Accordingly, the mesh stent will not only well align with the endogenous heart tissue but the contact area of mesh stent and endogenous tissue will be increased. In this way the mesh stent and prosthesis according to the disclosure achieves in improved fixation due to an improved friction because more surface of the stent or replacement heart valve is thus in contact with the endogenous surface of the endogenous valve surrounding tissue. The mesh stent according to the disclosure may advantageously achieve an adaptation of the a priori round mesh stent to an oval shaped endogenous heart valve geometry, and thus the stent or replacement heart valve prosthesis will exhibit improved fixation characteristics in situ. Improved fixation characteristics can also be achieved if the stent or replacement heart valve prosthesis achieves only a partial alignment with the endogenous tissue or endogenous ventricular tissue. Moreover, an interference of the loops with the cordae can contribute to an improved fixation characteristics of the prosthesis.

In one aspect the mesh stent according to the disclosure exhibit one or more reinforced areas, preferably wherein the reinforced area is located on the mesh stent area which, when deployed in the target site, will align essentially with the ventricular area of the target site, preferably in the context of a replacement heart valve of a tricuspid or mitral heart valve) or wherein the reinforced area is located on the mesh stent area which, when deployed in the target site, will align essentially with the aortic or pulmonary area of the target site, preferably in the context of a replacement heart valve of a aortic or pulmonary heart valve.

In one aspect in the mesh stent according to the disclosure the reinforced area is located on the mesh stent area in the outflow area of the mesh stent.

A mesh stent according to the disclosure can exhibit one or more reinforced areas wherein in one aspect the re-enforced area is characterized by a mesh double or triple layer, preferably made of a one part mesh, preferably characterized by back-loops. A back-loop is specifically formed. In a re-loading procedure the loop will flip over and thus can be pulled back into the catheter. and which forms an integral part of the mesh stent. A one part mesh can be used, preferably wherein the layers of the outer stent have the same three dimensional geometry and form a superimposed layer structure; in such a superimposed stent structure the various layers can contribute to the definition and design of the radial force in a particular stent area and thus contribute to a positive and advantageous spring or absorbing effect. The layers of the mesh stent can be connected to each other by useful means like sutures etc.

In one aspect the re-enforced area is characterized by a mesh double or triple layer which is further characterized by a space between the mesh layers or/and by a conical geometry of the two or three mesh layers, preferably wherein the conical geometry and/or the distance increases between the mesh layers in the proximal (inflow) direction.

The flexibility characteristics of the mesh stent according to the disclosure can be designed and adapted by way of the or a combination of the re-enforcement features wherein the re-enforced area is characterized by a reduced flexibility compared to a non-re-enforced mesh stent area or/and is characterized by an increased radial force compared to a non-re-enforced mesh stent area.

A mesh stent according to the disclosure can be characterized by three areas defined as a proximal area or atrium area or inflow area, a middle area or annulus area (or a sub-groove area), and a distal area or ventricular area or outflow area.

The invention advantageously can achieve a particular behavior of the prosthesis by way of defining and choosing the design features of the disclosure as a single feature or a combination of features and thus one can achieve a particular radial force distribution and thus achieve an improved fixation of the prosthesis at the implantation site.

In prior art replacement heart valve prostheses designs may exhibit a radial force distribution (over the length of the prosthesis) in the different area which is unfavorable for an optimized prosthesis fixation, particularly in the context of mitral or tricuspid replacement therapy. Prostheses according to the state of the art may exhibit distally a radial force being too high. This may thus lead—in situ after implantation and when the heart is beating—to the prosthesis being pushed gradually in proximal direction (i.e. in inflow direction) and a dislocation of the prosthesis.

The prosthesis according to the disclosure may now achieve by way of its re-enforcement features, e.g. a re-enforced area or a design wherein the distal part of the mesh is not connected with the inner stent, a different and improved radial force distribution and an improved fixation of the replacement heart valve prosthesis at the desired implantation site.

The additional design features like loops or/and an improved alignment of the outer mesh stent with the endogenous heart tissue in the ventricular area may contribute to such an improved fixation.

The mesh stent according to the disclosure will be designed in its dimensions as suitable for a particular patient or patient group, and the dimensions of the three prosthesis areas will be chosen as is most appropriate. In one aspect the prosthesis according to the disclosure will have prosthesis dimensions wherein the proximal area has a longitudinal dimension of 1 to 25 mm, preferably 1 to 5 mm, the middle area has a longitudinal dimension of 1 to 25 mm, preferably 4 to 10 mm, and the distal area has a longitudinal dimension of 1 to 25 mm, preferably 4 to 10 mm.

In another aspect the disclosure relates to a heart valve prosthesis comprising a mesh stent as described above (which is the first stent) and a second stent, wherein the first stent is the mesh stent (outer stent) and the second stent is the inner stent comprising a valve fixed thereto, preferably by one or more sutures.

In the heart valve prosthesis according the disclosure the inner stent is a laser cut Nitinol tube, wherein the inner stent has preferably an inner diameter of between 8 mm to 40 mm, or/and the inner stent has an outer diameter of between 9 mm to 41 mm, or 15 to 41 mm or/and the inner stent has a longitudinal dimension of 8 to 35 mm in its expanded configuration. The inner stent may be comprised of two, three, four, five or six rows of cells.

In the heart valve prosthesis according to the disclosure the two stents may be connected by suitable and generally known means by the skilled person. The inner stent may be connected with the outer stent preferably by one or more sutures or by way of one or more connecting structures. Such connecting structures may be clips or otherwise two part means which will remain stable once connected to each other.

In the heart valve prosthesis according to the disclosure the inner and outer stents can be connected and fixed to each other as is appropriate and useful for the function of the prosthesis and in addition as may be useful for the crimping procedure. In certain embodiments the inner stent is connected to the outer stent preferably on its distal area (the outflow area) and proximal area (the inflow area) or essentially on its proximal area or/and wherein the distal area of the outer stent is not connected with the inner stent.

In one aspect the heart valve prosthesis according to the disclosure is advantageous wherein the distal area (outflow area) of the outer mesh stent is not connected with the inner stent and wherein the angle of the outer mesh stent in relation to the inner stent is particularly chosen. In addition the angle alpha can be chosen in a specific dimension. All three design features will contribute to an improved fixation of the mesh stent and heart valve prosthesis at the implantation site. In a particular embodiment according to the disclosure the outer stent forms an angle with the inner stent of preferably of 5 to 90°, or 25° to 50°, more preferably of 35 to 45°.

Figure 1A:
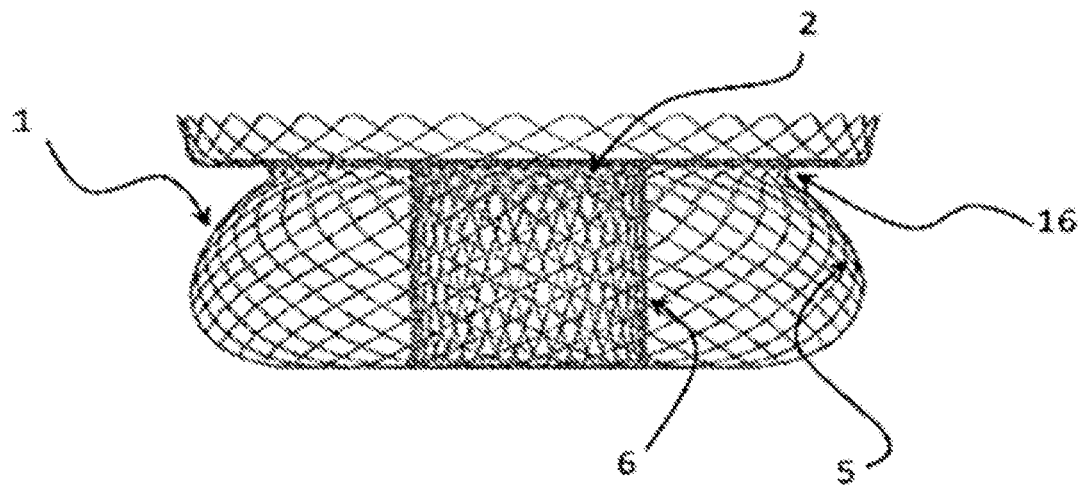
FIGS. 1a and 1b illustrate an example of a replacement heart valve prosthesis of the prior art composed of an laser cut tube inner stent (2) meant to carrying the valve and a braided outer stent (1), also denoted outer mesh stent, combined therewith for positioning and fixation of the prosthesis at the target site (two-part stent).
Figure 1B:
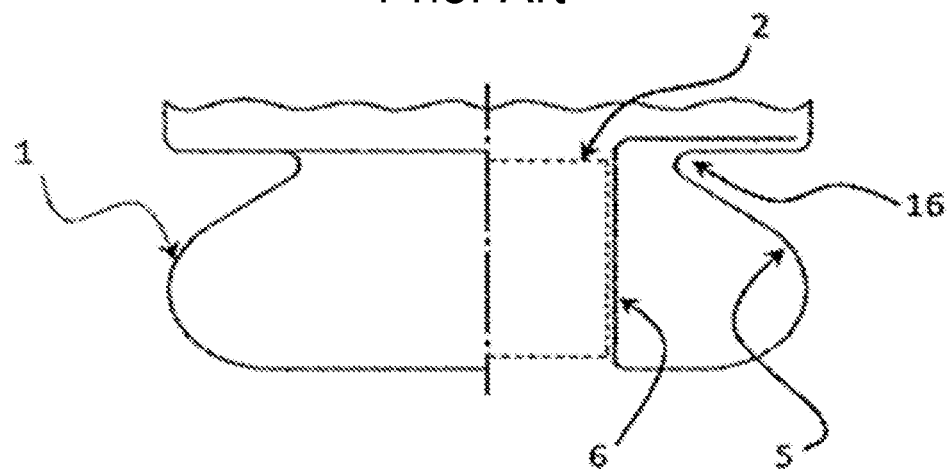
Figure 2A:
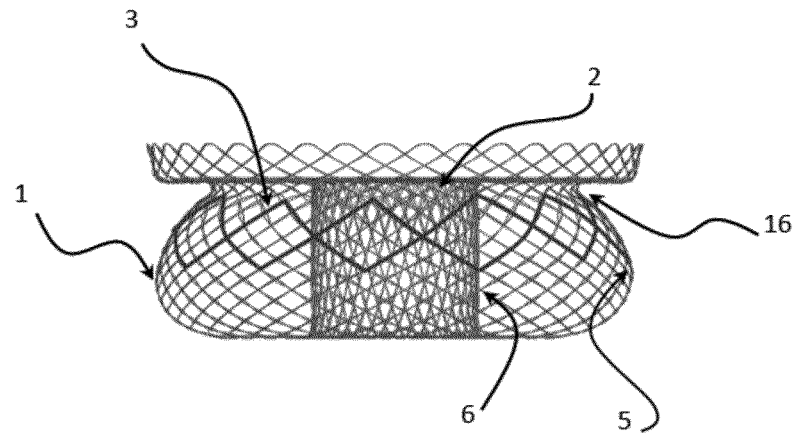
FIGS. 2a and 2b illustrate one aspect of the disclosure, i.e. a two-part stent as of FIG. 1 comprising a stabilizer means (3) located distally (which can also be seen as below) of a groove meant to support fixation at the annulus at the target site.
Figure 2B:
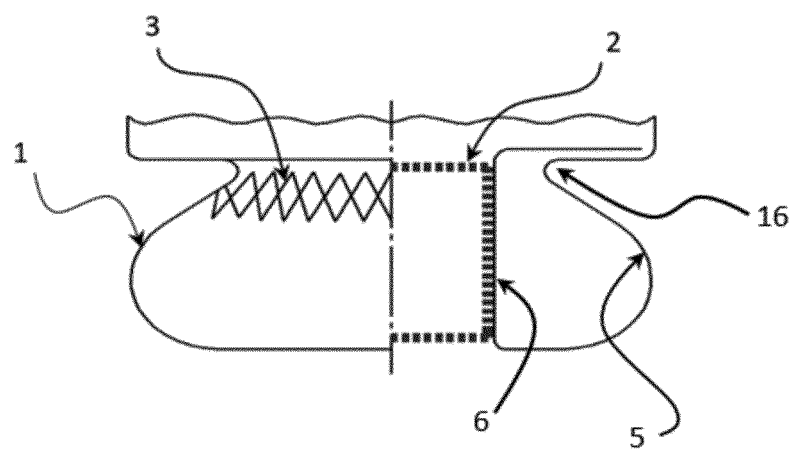
Figure 3A:
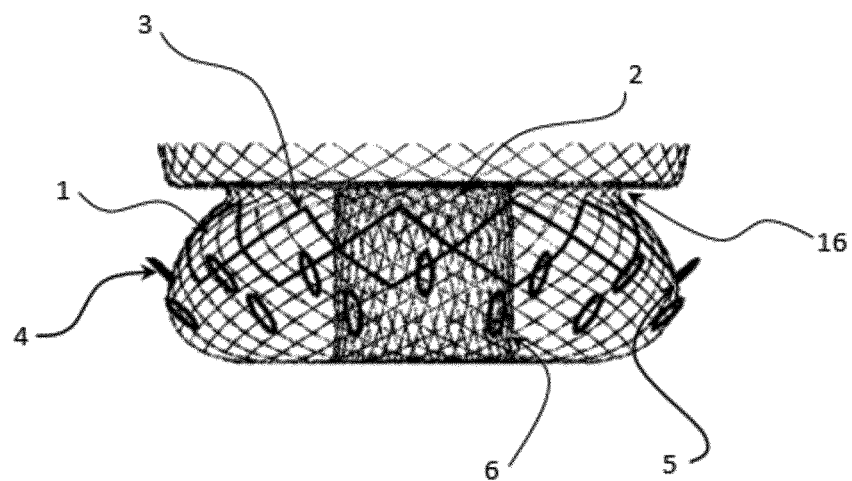
FIGS. 3a and 3b illustrate one aspect of the disclosure, i.e. a two-part stent as of FIG. 2 comprising in addition loops (4) for better fixation after implantation. In the embodiment as depicted (3a, 3b) the loops (4) are positioned below the groove of the outer stent and thus after implantation below the annulus in distal or outflow direction. The outer stent thus contributes to the fixation of the replacement heart valve prosthesis at the implantation site. The loops will contact the sub-annular or/and ventricular tissue and thus increase friction between the prosthesis and the implantation site providing for better fixation of the prosthesis at the implantation site. Additional improved fixation and friction can be exhibited by the loops of the prosthesis when the loops interfere with the chordae or/and the native heart valves and thus stabilize the prosthesis in place. The loops can exhibit varying angles with respect to the outer stent and thus also exhibit a radial force towards the heart tissue.
Figure 3B:
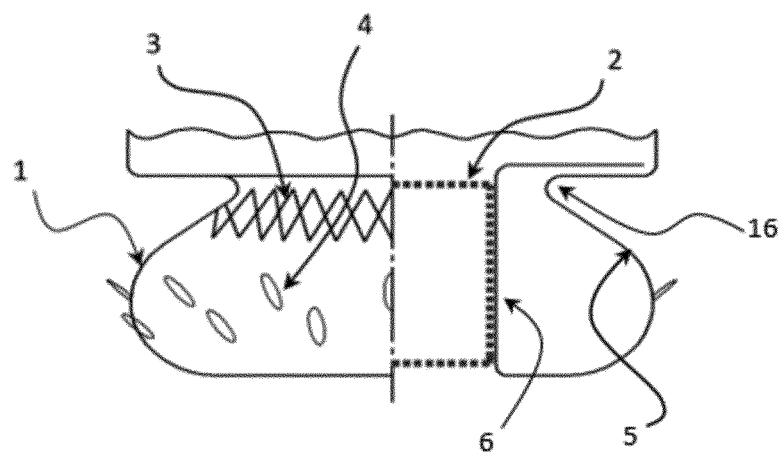
Figure 4:
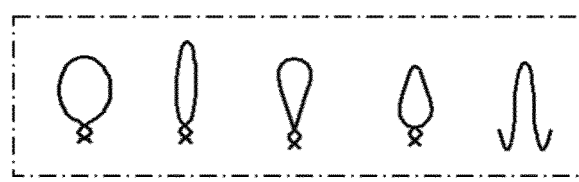
FIG. 4 illustrates one aspect of the disclosure, i.e. different types and shapes of loops.
Figure 5A:
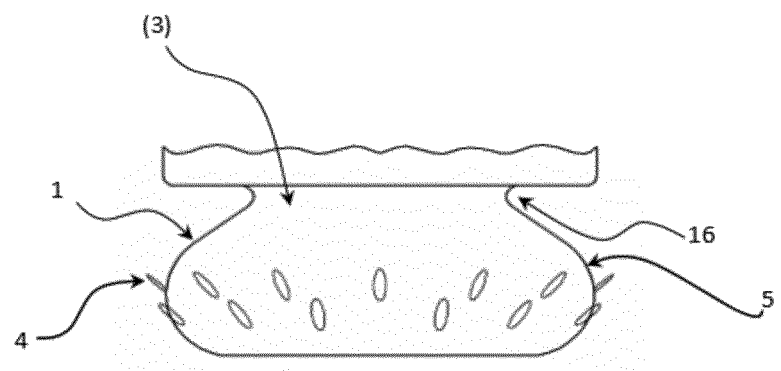
FIGS. 5a and 5b illustrate one aspect of the disclosure, i.e. loops (4) are positioned in the distal area of the braided outer stent (mesh stent); the outer stent is connected with the inner laser cut stent at the middle area; the outer stent is not connected with the inner stent at the distal area; the outer mesh (5) and inner mesh (6) of the outer mesh stent form in the middle or/and distal area a double layer which provides for stability or/and axial force which can be engineered as to the requirements of the particular case; in certain embodiments a stabilizer feature (like additional wires or/and twisted wires below the v-groove) are not present while in other embodiments according to the disclosure can be added to engineer stent stability and stent axial force.
Figure 5B:
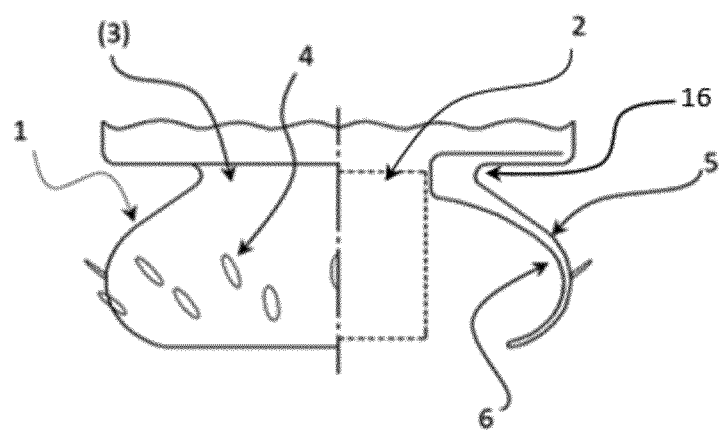
Figure 6A:
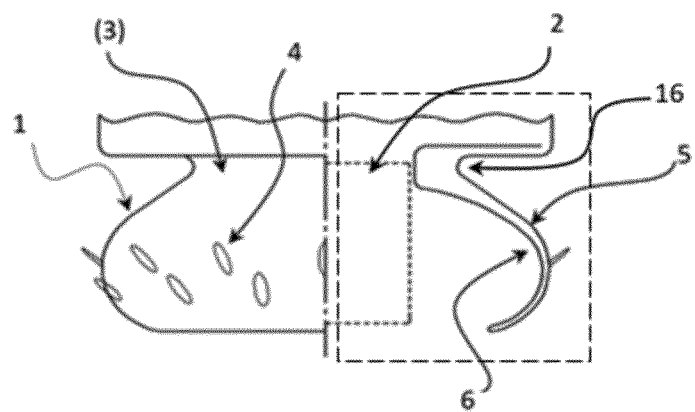
FIGS. 6a and 6b illustrate one aspect of the disclosure, i.e. a double stent prosthesis, wherein distally the outer stent (2) is not connected to the inner stent (1). The inner mesh (6) and outer mesh (5) are folded and oriented close to each other in the distal area. Moreover, the inner mesh (6) and outer mesh (5) form an angle ("angle structure" by way of two accessory lines drawn into the outer stent for illustration purposes) wherein the angle is marked as "alpha". "Alpha" is the area between the two arrow heads marked at the accessory lines in the Figure in direction axial to central in direction to the connection of inner stent (2) where both inner stent (2) and outer stent (1) are connected. The inner mesh (6) and outer mesh (5) thus form an angle which can be chosen depending on the stability and dimension requirements. The close orientation of the inner mesh (6) and outer mesh (5) in combination with the "angle alpha" imply a number of advantages as depicted in FIG. 6b. E.g. it implies the lack of connection of the inner stent (2) and outer stent (1) and thus it can produce distally a spring or absorbing effect and flexibility when the prosthesis is implanted. Moreover, this structure will lead to an advantageous flexibility when crimping the prosthesis into the catheter. The angle "alpha" can vary, e.g. from 5° to 90° or from 5° to 15°, and it will contribute or/and define the stability and radial force of the outer stent (1) relating to the fixation features of the prosthesis.
Figure 6B:
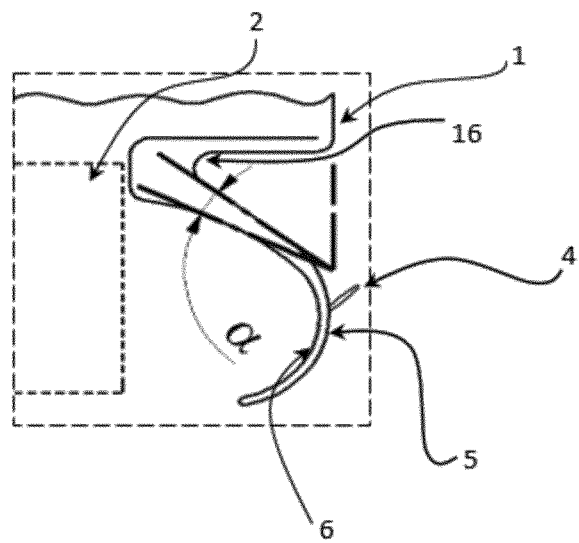
Figure 7:
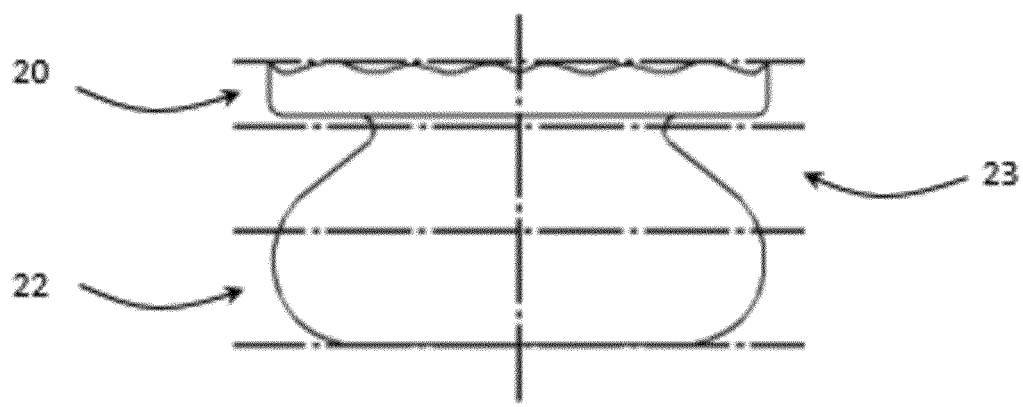
FIG. 7 illustrates one aspect of the disclosure, i.e. the prosthesis being defined into three areas, i.e. a proximal area (or inflow area), a middle area (or groove area, e.g. V- or U-groove, which can also be denoted sub-groove area) and a distal area (or outflow area). The groove area and the distal area can also be denoted sub-annular area. These areas may be adapted in their dimensions; accordingly, stability/flexibility features of the prosthesis may be engineered and the prosthesis may be adapted to the particular geometry of a target site and patient geometry and specifics.
Figure 8:
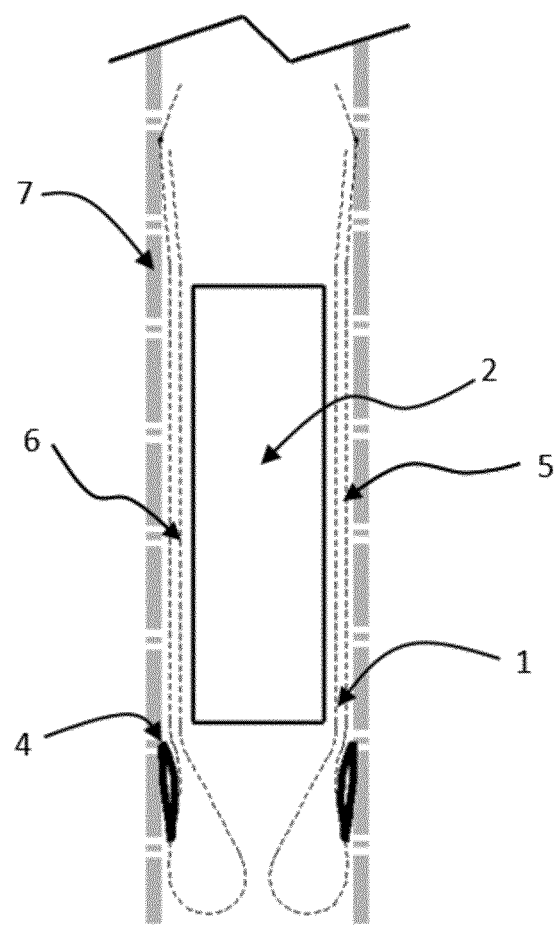
FIG. 8 illustrates one aspect of the disclosure, i.e. a prosthesis of the disclosure crimped into a loading part of a catheter for delivery through the vasculature of a patient. It shows that the loops (4) are positioned in a manner in order not to superimpose with the outer (5) and inner (6) mesh of the outer stent (1) or in an alternative in a manner in order not to superimpose with the inner stent (2) and thus provide for a low profile of the crimped prosthesis. In one aspect of the disclosure the loops (4) may be designed to flip over during the crimping/loading or re-loading procedure for an optimized positioning and low profile in the catheter. The loops thus can e.g. flip over essentially 180°, or up to 180°.

The heart valve prosthesis according to the disclosure may be deployed by way of a catheter system. It is usually desirable to achieve a low profile of the heart valve prosthesis loaded onto the catheter. Accordingly, in the heart valve prosthesis according to the disclosure in the crimped configuration in one embodiment the loops are positioned on the mesh stent in the ventricular area and so to be located on the mesh stent in the area wherein the mesh stent does not overlap with itself or/and in the area wherein the prosthesis exhibits one stent layer less in its crimped configuration. See e.g. FIG. 8.

In the mesh stent according to the disclosure or heart valve prosthesis according to the disclosure it was described above that the dimension can be chosen as will be most suitable for the use and an advantageous implantation and fixation. It was also described that the mesh areas can be adapted in their longitudinal dimensions. It is also possible to adapt the diameter of the mesh stent or heart valve prosthesis for improved fixation characteristics. Accordingly, the three areas of the mesh stent or heart valve prosthesis may exhibit different outer diameters, preferably the three outer diameters are in the range of 40 to 90 mm or of 20 to 90 mm in the expanded state of the stent. The outer diameters can be equal or different.

In one aspect the mesh stent according to the disclosure or heart valve prosthesis according to the disclosure is designed wherein the middle area exhibits an essentially smaller outer diameter than the other two areas and preferably forming a groove. Such a groove can be shaped essentially as V- or U-groove or any combination of such geometry in order to achieve an improved alignment with the endogenous heart tissue and geometry.

The overall mesh stent and heart valve prosthesis design according to the disclosure will lead to a specific radial force distribution in longitudinal dimension. In a particular embodiment the radial force in the sub-annular area is essentially equal or higher compared to the ventricular or outflow area of the mesh stent or prosthesis. The radial force over the prosthesis as disclosed herein is preferably as follows: proximal area (inflow area) to middle area to distal area (outflow area) equals 1-2 to 0.5-1 to 2-3.

In one aspect the mesh stent or heart valve prosthesis according to the disclosure exhibits a radial force in the annulus area in the range of 0.5 to 20 N, or 2 to 20 N. In the area of the Z-ring it can be 1 to 40 N or 15 to 40 N.

In another aspect the disclosure relates to a heart valve prosthesis as described above wherein the outer stent is a laser cut stent, preferably a Nitinol stent.

In one aspect the disclosure relates to a stent or a replacement heart valve prosthesis comprising or consisting of two laser cut Nitinol stents—an inner and outer stent—preferably connected by way of one or more connecting means or by way of a physical method like welding, and preferably having attached a valve to the inner stent.

A laser cut inner stent connected to a laser cut outer stent according to the disclosure advantageously achieves a good long time fixation at the target site and at the same time provides for a good replacement heart valve function. Advantageously longitudinal motion of the inner stent with regard to the outer stent is avoided. Also longitudinal motion of the replacement heart valve prosthesis is essentially avoided which contributes to a correct functionality of the replacement heart valve prosthesis.

The combination of the two laser cut stents according to the disclosure advantageously provides for an advantageous crush resistance of the prosthesis and thus superior functionality of the replacement heart valve.

An issue of replacement heart valve prostheses is a folding of stent parts during deployment at the target site.

The particular design of the replacement heart valve prosthesis according to the disclosure achieves to essentially avoid said problem.

The replacement heart valve prosthesis can be divided longitudinally into three areas: firstly, a proximal area or inflow area or atrium area. Secondly, a middle area or preferably a groove area or annular area. Thirdly, a distal area or outflow area or sub-annular area. The different areas will be designed to best fit a particular endogenous heart valve geometry and its dimensions. The three areas can have the following dimensions:

proximal area: 1 mm-25 mm, diameter 20-90 mm, stent cell number circumferentially 6-48, preferably 10-18;
middle area: 1 mm-25 mm, diameter 10-80, stent cell number circumferentially 6-48, preferably 10-18;
distal area: 1 mm-35 mm, diameter 20-90, stent cell number circumferentially 6-48, preferably 10-18.

In one aspect the disclosure relates to a heart valve prosthesis as described above wherein the laser cut outer stent is characterized by at least 4 loops and/or anchoring cells, preferably 6 to 18, 8 to 12 or 10 loops and/or anchoring cells. The laser cut outer stent may be characterized circumferentially by a defined number of cells in the different stent areas. The laser cut outer stent according to the disclosure may be characterized by 14 to 22 or 16 to 18 cells (also denoted support cells) in the proximal area and by 14 to 22 or 16 to 18 cells in the distal area. The distal area may comprise or be composed of one, two, three, four or five rows of cells. In embodiments wherein the distal area is composed of two or more rows of cells the number of circumferential cells is 16 to 34 or 18 to 28 to cells.

The laser cut inner stent may be characterized by two, three, four, five, or six rows of cells. Circumferentially the inner stent may comprise or be composed of 4 to 24, or 10 to 30 or 14 to 20 or 16 to 18 cells in each row.

The laser cut outer stent may comprise eyelets at the proximal end of one or more or all cells which may serve for easier loading into the catheter for deployment.

A laser cut outer stent according to the disclosure distally not connected with the inner stent also contributes to the advantageous compliance functionality of the prosthesis according to the disclosure.

A replacement heart valve prosthesis according to the disclosure will be characterized in situ by advantageous radial force distribution which leads to an advantageous fixation in the implantation site. A prosthesis according to the disclosure will be characterized by essentially no or by only little movement in the atrium area. In the ventricular area it will be characterized by a advantageous flexibility and/or compliance contributing to an improved fixation and long term functioning.

The designs according to the above disclosure also imply the advantage that stent areas prone to potential stent breaks and damages are avoided. E.g. the distal outer part or/and end exhibits an open geometry. Thus, in the prosthesis according to the disclosure in comparison to a closed design wherein the outer distal stent is connected with the inner distal part of the inner stent no stent breaks may occur.

Replacement heart valve prostheses as described above exhibit advantageous fixation characteristics wherein the outer stent comprises loops in the outflow area, preferably on the cells on its outflow end (distal end). In an embodiment the prosthesis is preferably characterized by at least two anchoring cell, e.g. 4 to 48, or 4 to 20 anchoring cells. The prosthesis can also comprise in addition loops as integral part of the laser cut stent or fixed thereto in any useful manner.

In replacement heart valve prostheses as described above the loops may be positioned in the most distal cells and the loops may protrude outwardly and exhibit flexibility in inward direction.

Figure 23:
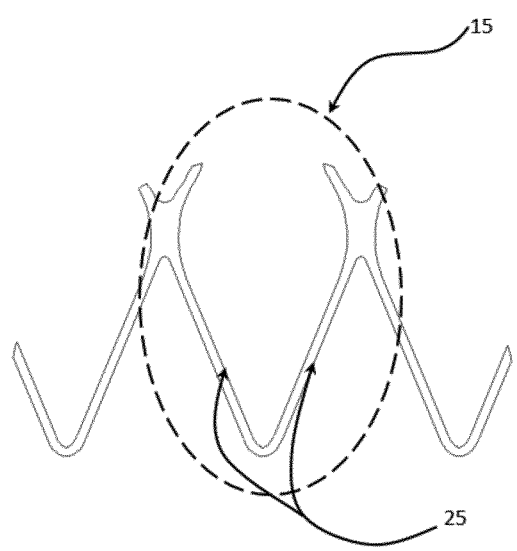
Figure 24:
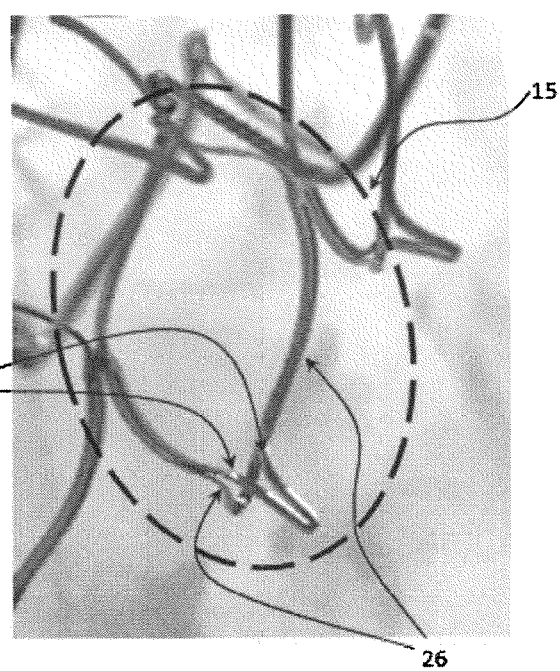

An embodiment according to the disclosure comprising anchoring is depicted in FIGS. 22 to 24. Such anchoring cells advantageously contribute to an improved fixation of the replacement heart valve prosthesis in the target site and in an atraumatic manner. The loop positioned within a support cell of the outer stent exhibits the advantage that it provides for friction and interference with the tissue increasing a proper fixation of the prosthesis in the target site after implantation.

An advantage of the integrality of the anchoring cells and loops comprised therein is that no addition of material or means is necessary to be added in an addition production step and also in terms of durability of the prosthesis it lifespan may be increased and not be prone to potential stent breaks.

The loop according to the above disclosure can be formed in a manner that in addition the loops point outwardly and thus support its fixation purpose.

The outer stent can comprise e.g. 4 to 48, or 4 to 20, 8 to 16 or 10 to 12 anchoring cells wherein the anchoring cells are either positioned in one row circumferentially at the distal area or outflow end of the prosthesis. The anchoring cells can also be positioned in e.g. two rows in alternating positions in the outer stent.

One anchoring cell according to the above disclosure can have a diameter of 3 to 25 mm, or 3 to 20, or 3 to 10 mm, or 3 to 5 mm.

A replacement heart valve prosthesis as described above may have the inner and outer stent connected with a connecting means or in a direct manner using e.g. a physical method like welding, or by way of one or more sutures, one or more screws, or one or more clipping means.

The outer stent can also comprise in defined areas or positions S-struts. The S-struts may be combined with the connecting means and one or two S-struts may be positioned at each side of a connecting means. The S-struts and connecting means are positioned so that the commissures of the replacement heart valve is not in the same level but displaced by an angle ß. Two connecting means or/and two or four S-struts are located in between the commissures of the replacement heart valve. Thus they contribute to an advantageous crush resistance. Also the disfavored folding of the stent may thus be prevented. Finally, also the coaptation functionality of the valve leaflets of the replacement heart valve is thus improved or maintained.

The S-strut element implies various advantages. It may provide for easier form shaping during production and also imply advantages during the crimping procedure when loading the prosthesis onto the catheter for delivery. Moreover, materials tensions within the prosthesis are reduced, punctual stress is reduced and the fatigue behavior is improved.

Heart valve prosthesis as described above wherein the clipping means is characterized by interconnecting means and a securing means like a sleeve.

The connection of inner and outer stent by use of one or more clipping means was not obvious nor the advantages and the particular positioning of said clipping means in the area of the atrium. The finding of the inventors to place said clipping means in this area has the advantage that during heart beat and when the implanted prosthesis is exposed to stress the environment where the clipping means are positioned is exposed to less stress as compared to the e.g. the ventricular environment of the heart. This it could be achieved that the clipping means is subject to less stress and thus less the life span and fatigue of the implanted prosthesis is positively influenced. Moreover, the clipping means represent relatively much and dense material which facilitated to visualize the area of the prosthesis which is meant to be positioned in the annulus area. Thus it is possible to direct and position the prosthesis correctly without the need of opaque markers like gold, tantalum, platinum-iridium.

In an advantageous embodiment the valve commissures (or posts carrying the valve or connected to the valve) of the replacement heart valve prosthesis located in the inner stent are positioned between the connecting struts or/and connecting means, like the clipping means.

These prosthesis structures may advantageously be positioned in a certain distance or angle. Thus it can advantageously be achieved to have an optimized coaptation of the valve leaflets of the prosthesis and to avoid inefficient replacement heart valve prosthesis function. Moreover, in this manner the deformation of the inner stent carrying the valve due to the heart beating and tissue movement is reduced and kept at a possible minimum. This also contributes to a correct replacement heart valve prosthesis function after implantation.

Thus and by way of this structural design feature a cooperative or synergistic effect with regards to inner stent stability and reduction of shape change can be achieved supporting a correct opening and closure of the valve leaflets connected to the inner stent.

The crush resistance should be optimized with regard to the endogenous heart structures and functionally related behavior of the implanted prosthesis. One goal achieved with the prosthesis as disclosed herein is that the implanted prosthesis cooperates or/and shows an advantageous compliance with the endogenous tissue and the heart beat requirements and thus the prosthesis as disclosed herein is safely positioned and fixed for long term correct functioning and at the same time as little as possible interference with the endogenous heart structures.

The replacement heart valve prosthesis comprising two laser cut stents connected to each other, preferably by a connecting means, advantageously achieves to providing a combination of an inner stent with high crush resistance with a good valve function, and wherein the outer stent exhibits particularly in the outflow region a low crush resistance and thus advantageously does only little interfere with the ventricular heart areas. Thus the prosthesis as disclosed herein exhibits a high crush resistance in the inner stent and a low crush resistance in the outer stent. In fact by way of the inventive design of the prosthesis of the disclosure the outer stent adapts to the natural endogenous ventricular geometry without too much of an impact on the ventricular geometry.

This positive interaction with the endogenous heart tissue and structure and even be improved by the above described elements like S-struts which may be combined with the connecting struts and the clipping means. These elements together with the specific placement and orientation of the commissures provides for an advantageous functionality. The inclusion of anchoring cells in the distal area of the prosthesis and their atraumatic design reduce or avoid tissue damage and at the same time allow for improved fixation and long term fixation of the prosthesis after implantation. The combination and positioning of the connecting means will advantageously avoid or limit the longitudinal movement of the inner stent as described herein.

Moreover, the prosthesis as disclosed herein will exhibit advantageous fixation features and characteristics and in a three-part stent the specific combination of connecting struts and connecting strut guide will provide for a longitudinal movement limitation during systolic contraction of the heart. The three-way connection of connecting struts and connecting strut guide and connecting means and its positioning proximal from the inner stent will essentially prevent or limit longitudinal movement of the inner stent when the valve is closed. The connecting strut guide can have a eyelet, V or U shape wherein the eyelet shape is preferred. An eyelet shape will advantageously keep all parts in a predefined position allowing only little movement and maintaining a predefined geometry during replacement heart valve function.

One aspect of the disclosure is also a replacement heart valve prosthesis as described above wherein the inner and outer stent is connected with 4 to 20 connecting means, preferably with 6 to 14, or 8 to 18, or 8 to 12.

In a replacement heart valve prosthesis as described above the prosthesis can be crimped to a diameter of 16 to 40 French, or of 18 to 30, or of 16 to 35 French, or of 20 to 35 French, or of 25 to 35 French.

The replacement valve is connected to the inner stent and usually is composed of three leaflets produced according to the state of the art in one or three pieces and sutured into the inner stent. The material can be chosen form any known and useful materials as e.g. bovine or porcine pericard, polymer materials etc. which do not need to be described in more detail here as the materials and their preparation are well known in the art. The prosthesis may comprise covers and sealing as it is appropriate for its functioning.

It is an advantage that in any prosthesis size wherein the outer stent size may vary, the inner stent carrying the replacement valve may always have the same diameter and dimensions which facilitates the production and reduces production cost.

One advantageous concept in common to all variations and embodiments as disclosed herein is an outer stent with improved fixation characteristics which at the same time decouples or isolates or protects the inner stent essentially from deformation or impact with regard to the inner stent or/and valve geometry and thus combines improved fixation characteristics with improved replacement valve functionality.

One advantage of a laser cut stent in laser cut stent of a replacement heart valve prosthesis according to the disclosure is that there exist very advanced know how as to production and thus such a prosthesis can be manufactured in a very cost efficient manner.

Also the production process is easily controllable when manufacturing a laser cut stent and thus from a cost and quality control aspect it implies advantages.

The disclosure relates to various stent embodiments wherein the stent can be a two-part stent characterized by a laser cut inner stent connected to an outer mesh stent or a laser cut inner stent connected to a laser cut outer stent (two-part or three-part stent) wherein the outer stent may comprise additional features. In all embodiments and variations as described herein the goal of an improved fixation at the target site is achieved with a varying number of features or combinations of features. Thus the current disclosure provides a variation of different advantageous solution solving the same problem of an improved fixation of a replacement heart valve, preferably in the context of a tricuspid or mitral heart valve. Moreover the current disclosure relates to providing a number of means useful for the improved fixation of a replacement heart valve prosthesis at its target site.

In another aspect the disclosure relates to the use of the described replacement heart valve for use in a replacement heart valve therapy or a method of implantation thereof. The replacement heart valve prosthesis as described herein can be delivered and implanted with known catheter techniques to a desired target site, e.g. to replace a tricuspid heart valve, in a patient. A route of delivery and deployment is e.g. a transfemoral (percutaneous) catheter implantation.

In another aspect the disclosure relates to a method for implantation of a heart valve prosthesis as described above wherein the prosthesis is delivered, e.g. transfemoral, using a catheter comprising the steps of loading the prosthesis onto the catheter, introducing the catheter in an individual, moving the catheter tip to the target site and deploying the prosthesis.

In another aspect the disclosure relates to a connecting means for stents characterized by an interlocking yoke, an interlocking nail or teeth and a sleeve wherein the interlocking yoke, nail or/and teeth, preferably a connecting strut guide, connect two or three connecting struts, preferably in a releasable manner.

It shall be understood that each of the single features as described herein are meant to be combinable in any possible manner or combination, and that specific embodiments as described in the figures or in the above description in a certain feature combination shall not be interpreted as being limiting solely to said combination and that the specific embodiments as describe herein are not meant to be limiting for the scope of the disclosure.

REFERENCE NUMBER LIST

1—wire braided outer stent (mesh stent)
2—laser cut inner stent
3—stabilizer (e.g. additional wires and/or twisted wires below v-groove)
4—loops
5—outer mesh
6—inner mesh
7—catheter
8—S-strut
9—interlocking nail
10—sleeve
11—laser cut outer stent
11a-proximal laser cut outer stent (stent part)
11b-distal laser cut outer stent (stent part)
12, 12'—connecting struts
13—connection inner/outer stent
14—interlocking teeth
15—anchoring cell
16—v-groove
17—connecting strut guide
18—interlocking yoke
19—connecting means
20—proximal area
21—commissure
22—distal area
23—middle area
24—valve leaflet
25—loop struts
26—RF-struts
27—Z-ring
28—folding
29—right ventricle
30—tricuspid heart valve
31—annulus
32—chordae
33—drops
34—open cell
35—closed window
36—drop strut width (e.g. 0.05 mm-0.9 mm)
37—drop strut length (e.g. 0.15 mm-25 mm)
38—drop diameter (e.g. 0.25 mm-5 mm)

The invention claimed is:

1. A prosthesis comprising an outer stent that is a laser cut stent and an inner stent that is a laser cut stent, wherein:
   (i) the outer stent comprises a proximal outer stent region and a distal outer stent region, wherein the distal outer stent region comprises a connecting strut guide;
   (ii) the proximal outer stent region comprises a connecting strut and the inner stent comprises a connecting strut, wherein the connecting strut of the proximal outer stent region and/or the connecting strut of the inner stent is an S-strut;
   (iii) the outer stent and the inner stent form a double layer that provides for crush resistance; and
   (iv) the connecting strut of the inner stent and the connecting strut of the proximal outer stent region are connected by a connecting means, and
wherein, when implanted, the connecting strut guide is configured to slidably connect to the connecting strut of the inner stent, thereby connecting the inner stent, the proximal outer stent region, and the distal outer stent region in a proximal area of the prosthesis.

2. The prosthesis according to claim 1, wherein the prosthesis comprises a proximal end, a middle area, and a distal end, and wherein:
   a) the proximal end of the prosthesis has a longitudinal dimension of 1 to 25 mm, the middle area of the prosthesis has a longitudinal dimension of 1 to 25 mm, and the distal end of the prosthesis has a longitudinal dimension of 1 to 25 mm;
   b) the proximal end, middle area, and distal end of the prosthesis have different outer diameters in an expanded state of the prosthesis;
   c) the middle area of the prosthesis has a smaller outer diameter than an outer diameter of the proximal and distal ends of the prosthesis;
   d) a radial force in a sub-annular area of the prosthesis is equal to or higher than a radial force in a ventricular or outflow area of the prosthesis; or
   e) a radial force of an annular area and/or the distal area of the prosthesis is in a range of 0.5 to 20 N.

3. The prosthesis according to claim 2, wherein:
   a) the longitudinal dimension of the proximal area is from 1 to 5 mm, the longitudinal dimension of the middle area is from 4 to 10 mm, and the longitudinal dimension of the distal area is from 4 to 10 mm;
   b) the outer diameter of the proximal, middle, and distal areas are in a range of 40 to 90 mm or 20 to 90 mm in the expanded state of the prosthesis; and/or
   c) the middle area forms a groove.

4. The prosthesis of claim 1, further comprising a valve fixed thereto, thereby forming a heart valve prosthesis.

5. The prosthesis according to claim 4, wherein the valve is fixed to the prosthesis by one or more sutures.

6. The prosthesis according to claim 4, wherein the inner stent:
   a) has an inner diameter of between 8 mm and 40 mm;
   b) has an outer diameter of between 15 mm and 41 mm; and/or
   c) comprises an expanded configuration, wherein the inner stent has a longitudinal dimension of 8 to 35 mm in the expanded configuration.

7. The prosthesis according to claim 4, wherein:
a) the outer stent forms an angle with the inner stent;
b) the outer stent is a nitinol stent;
c) the prosthesis can be crimped to a diameter of 16 to 40 French, 16 to 35 French, 20 to 35 French, or 25 to 35 French; and/or
d) the prosthesis is configured for deployment by way of catheter delivery.

8. The prosthesis according to claim 7, wherein:
a) the angle formed by the outer stent with the inner stent is 5 to 90°, 25 to 50°, or 35 to 45°; and/or
b) the catheter delivery is transfemoral catheter delivery.

9. The prosthesis according to claim 7, wherein:
a) the outer stent is characterized by 10 to 30 cells circumferentially in the proximal and/or distal area and/or the inner stent is characterized by 4 to 30, 4 to 24, or 10 to 30 cells circumferentially in three, four, or five rows.

10. The prosthesis according to claim 1, wherein the connecting means is or comprises one or more sutures, a welding, one or more screws, or one or more clips.

11. The prosthesis according to claim 10, wherein the one or more clips are characterized by an interlocking tooth and an interlocking yoke and a cover.

12. The prosthesis according to claim 1, wherein the inner stent and the proximal outer stent region are connected with 4 to 24 combinations of connecting struts and connecting means and wherein the distal outer stent region comprises one connecting strut guide for each of the connecting struts of the inner stent.

13. The prosthesis according to claim 12, wherein each of the inner stent and the proximal outer stent region comprises 6 to 14, 8 to 18, 8 to 12, or 12 of the connecting struts that are joined by the connecting means.

14. A method of replacement heart valve therapy comprising implanting the heart valve prosthesis according to claim 4 in a subject in need thereof.

15. The method of claim 14, wherein the heart valve prosthesis is delivered using a catheter, wherein the method further comprises loading the heart valve prosthesis onto the catheter, introducing the catheter into the subject, moving the catheter to a target site, and deploying the heart valve prosthesis at the target site.

16. The method of claim 15, wherein the heart valve prosthesis is delivered by transfemoral delivery.

17. The prosthesis of claim 1, wherein the connecting means releasably joins the inner stent and the outer stent.

18. The prosthesis of claim 17, wherein the connecting means comprises one or more sutures, a welding, one or more screws, or one or more clips.

19. The prosthesis of claim 1, wherein the outer stent further comprises a middle area and a distal area, wherein the middle area and/or the distal area comprise a circumferential stabilizer positioned inside and/or outside the outer stent.

20. The prosthesis of claim 19, wherein the circumferential stabilizer (i) is in a bent, zig-zag, or undulating geometry and/or (ii) is interwoven in the middle area of the outer stent and/or the distal area of the outer stent.

\* \* \* \* \*